US006962815B2

(12) United States Patent
Bartlett

(10) Patent No.: US 6,962,815 B2
(45) Date of Patent: Nov. 8, 2005

(54) AAV2 VECTORS AND METHODS

(75) Inventor: Jeffrey S. Bartlett, Worthington, OH (US)

(73) Assignee: Children's Hopital Inc., Columbus, OH (US)

(*) Notice: Subject to any disclaimer, the term of this patent is extended or adjusted under 35 U.S.C. 154(b) by 34 days.

(21) Appl. No.: 10/038,972

(22) Filed: Jan. 4, 2002

(65) Prior Publication Data

US 2002/0192823 A1 Dec. 19, 2002

Related U.S. Application Data

(60) Provisional application No. 60/260,124, filed on Jan. 5, 2001.

(51) Int. Cl.$^7$ .................. C12N 15/63; C12N 15/00; A01N 63/00; A61K 39/12; C07H 21/02

(52) U.S. Cl. .................. 435/455; 435/456; 435/320.1; 435/69.1; 435/91.41; 424/93.2; 424/199.1; 536/23.1; 800/3

(58) Field of Search .................. 424/93.2, 199.1; 435/455, 456, 235.1, 320.1, 69.1, 91.41; 536/23.1; 530/300; 800/3

(56) References Cited

FOREIGN PATENT DOCUMENTS

WO    WO00/28004    5/2000

OTHER PUBLICATIONS

Chiorini et al. Cloning of Adeno–Associated Virus Type 4 (AAV4) and Generation of Recombinant AAV4 Particles. Journal of Virology. p. 6823–6833, Sep. 1997.*

Kronenberg et al, Electron cryo–associated microscopy and image reconstruction of adeno–associated virus type 2 empty capsids, 2001, EMBO reports, vol. 21 (11) pp. 997–1002.*

Srivastava, et al., Nucleotide Sequence and Organization of the Adeno–Associated Virus 2 Genome, *Journal of Virology* 45 (2): 555–564 (Feb. 1983).

Ruffing et al., Mutations in the carboxy terminus of adeno–associated virus 2 capsid proteins affect viral infectivity: lack of an RGD integrin–binding motif, *Journal of General Virology* 75: 3385–3392 (1994).

Hermonat et al., Genetics of Adeno–Associated Virus: Isolation and Preliminary Characterization of Adeno–Associated Virus Type 2 Mutants, *Journal of Virology* 51 (2): 329–339 (Aug. 1984).

Santiago et al., New DNA enzyme targeting Egr–1 mRNA inhibits vascular smooth muscle proliferation and regrowth after injury, *Nature Medicine* 5 (11): 1264–1269 (Nov. 1999).

Muzyczka, Use of Adeno–Associated Virus as a General Transduction Vector for Mammalian Cells, *Current Topics in Microbiology and Immunology* 158: 97–129 (1992).

Girod et al., Genetic capsid modifications allow efficient re–targeting of adeno–associated virus type 2, *Nature Medicine* 5 (9): 1052–1056 (Sep. 1999).

Rabinowitz et al., Insertional Mutagenesis of AAV2 Capsid and the Production of Recombinant Virus, *Virology* 265: 274–285 (1999).

Tsao et al., The Three–Dimensional Structure of Canine Parvovirus and Its Functional Implications, *Science* 251: 1456–1464 (Mar. 1991).

Wu et al., The Canine Parvovirus Empty Capsid Structure, *J. Mol. Biol.* 233 (2): 231–244 (1993), Agbandje et al., Structure Determination of Feline Panleukopenia Virus Empty Particles, *Proteins* 16: 155–171 (Jun. 1993).

Agbandje–McKenna et al., Functional implications of the structure of the murine parvovirus, minute virus of mice, *Structure* 6 (11): 1369–1381 (Nov. 1998).

Llamas–Saiz et al., Structure Determination of Minute Virus of Mice, *Acta Crystallographica Section D* D53: 93–102 (1997).

Chipman et al., Cryo–electron microscopy studies of empty capsids of human parvovirus B19 complexed with its cellular receptor, *Proc. Natl. Acad. Sci. USA* 93: 7502–7506 (Jul. 1996).

McKenna et al., Three–Dimensional Structure of Aleutian Mink Disease Parvovirus: Implications for Disease Pathogenicity, *Journal of Virology* 73 (8): 6882–6891 (Aug. 1999).

Wu et al., Mutational Analysis of the Adeno–Associated Virus Type 2 (AAV2) Capsid Gene and Construction of AAV2 Vectors with Altered Tropism, *Journal of Virology* 74 (18): 8635–8647 (Sep. 2000).

Shi et al., Insertional Mutagenesis of the Adeno–Associated Virus Type 2 (AAV2) Capsid Gene and Generation of AAV2 Vectors Targeted to Alternative Cell–Surface Receptors, *Human Gene Therapy*, 12: 1697–1711 (Sep. 2001).

Bartlett et al., Infectious Entry Pathway of Adeno–Associated Virus and Adeno–Associated Virus Vectors. *Journal of Virology*, 74(6): 2777–2785 (1999).

Kigawa et al., Adenovirus–mediated Transfer of a p53 Gene in Ovarian Cancer, *Adv. Exp. Med. Biol.* 465(14): 207–14 (2000).

(Continued)

*Primary Examiner*—Terry McKelvey
*Assistant Examiner*—Maria Marvich
(74) *Attorney, Agent, or Firm*—Marshall, Gerstein & Borun LLP

(57) ABSTRACT

The invention relates to Adeno-associated virus vectors. In particular, it relates to Adeno-associated virus vectors with modified capsid proteins and materials and methods for their preparation and use.

25 Claims, No Drawings

OTHER PUBLICATIONS

Song et al., In vivo Studies of Adenovirus–mediated p53 Gene Therapy for Cis–platinum–Resistant Human Ovarian Tumor Xenografts, *Oncol. Res.*, 11(3): 153–159m (1999).

Yamaguchi et al., Co–transfection of Herpes Simplex Virus Thymidine Kinase Gene and Human Interleukin–2 Gene into Mouse Ovarian Cancer Cell Line, OVHM, *Intl. J. Mol. Med.*, 6(2): 185–190 (2000).

Genbank Accession No. AF043303, Adeno–Associated Virus 2 (Feb. 24, 1998).

Wu et al., "Mutational Analysis Of The Adano–Associated Virus Type 2 (AAV2) Capsid Gene And Construction of AAV2 Vactors With Altered Tropism," *Journal Of Virology*, 74(18): 8635–8647 (Sep. 2000).

* cited by examiner

SEQUENCE LISTING

<160> NUMBER OF SEQ ID NOS: 18

<210> SEQ ID NO 1
<211> LENGTH: 14
<212> TYPE: PRT
<213> ORGANISM: Artificial Sequence

```
<220> FEATURE:
<223> OTHER INFORMATION: RGD Peptide

<400> SEQUENCE: 1

Thr Gly Cys Asp Cys Arg Gly Asp Cys Phe Cys Gly Leu Ser
1               5                   10

<210> SEQ ID NO 2
<211> LENGTH: 11
<212> TYPE: PRT
<213> ORGANISM: Artificial Sequence
<220> FEATURE:
<223> OTHER INFORMATION: Bovine Papilloma Virus Peptide

<400> SEQUENCE: 2

Thr Gly Thr Pro Phe Tyr Leu Lys Gly Leu Ser
1               5                   10

<210> SEQ ID NO 3
<211> LENGTH: 15
<212> TYPE: PRT
<213> ORGANISM: Artificial Sequence
<220> FEATURE:
<223> OTHER INFORMATION: Luteinizing hormone Peptide

<400> SEQUENCE: 3

Thr Gly His Cys Ser Thr Cys Tyr Tyr His Lys Ser Gly Leu Ser
1               5                   10                  15

<210> SEQ ID NO 4
<211> LENGTH: 11
<212> TYPE: PRT
<213> ORGANISM: Artificial Sequence
<220> FEATURE:
<223> OTHER INFORMATION: Bovine Papilloma Virus Peptide

<400> SEQUENCE: 4

Thr Gly Thr Pro Phe Tyr Leu Lys Ala Leu Ser
1               5                   10

<210> SEQ ID NO 5
<211> LENGTH: 11
<212> TYPE: PRT
<213> ORGANISM: Artificial Sequence
<220> FEATURE:
<223> OTHER INFORMATION: Bovine Papilloma Virus Peptide

<400> SEQUENCE: 5

Thr Gly Thr Pro Phe Tyr Leu Lys Leu Leu Ala
1               5                   10

<210> SEQ ID NO 6
<211> LENGTH: 8
<212> TYPE: PRT
<213> ORGANISM: Artificial Sequence
<220> FEATURE:
<223> OTHER INFORMATION: Bovine Papilloma Virus Peptide

<400> SEQUENCE: 6

Thr Gly Thr Pro Phe Tyr Leu Lys
1               5

<210> SEQ ID NO 7
<211> LENGTH: 5
<212> TYPE: PRT
<213> ORGANISM: Artificial Sequence
<220> FEATURE:
```

-continued

<223> OTHER INFORMATION: Synthetic Linker Peptide

<400> SEQUENCE: 7

Thr Gly Ala Leu Ser
1               5

<210> SEQ ID NO 8
<211> LENGTH: 5
<212> TYPE: PRT
<213> ORGANISM: Artificial Sequence
<220> FEATURE:
<223> OTHER INFORMATION: Synthetic Linker Peptide

<400> SEQUENCE: 8

Thr Gly Leu Leu Ala
1               5

<210> SEQ ID NO 9
<211> LENGTH: 5
<212> TYPE: PRT
<213> ORGANISM: Artificial Sequence
<220> FEATURE:
<223> OTHER INFORMATION: Synthetic Linker Peptide

<400> SEQUENCE: 9

Thr Gly Gly Leu Ser
1               5

<210> SEQ ID NO 10
<211> LENGTH: 9
<212> TYPE: PRT
<213> ORGANISM: Artificial Sequence
<220> FEATURE:
<223> OTHER INFORMATION: 4C-RGD Peptide

<400> SEQUENCE: 10

Cys Asp Cys Arg Gly Asp Cys Phe Cys
1               5

<210> SEQ ID NO 11
<211> LENGTH: 15
<212> TYPE: PRT
<213> ORGANISM: Artificial Sequence
<220> FEATURE:
<223> OTHER INFORMATION: Biotin acceptor peptide

<400> SEQUENCE: 11

Gly Leu Asn Asp Ile Phe Glu Ala Gln Lys Ile Glu Trp His Glu
1               5                   10                  15

<210> SEQ ID NO 12
<211> LENGTH: 4679
<212> TYPE: DNA
<213> ORGANISM: adeno-associated virus 2

<400> SEQUENCE: 12
ttggccactc cctctctgcg cgctcgctcg ctcactgagg ccgggcgacc aaaggtcgcc      60
cgacgcccgg gctttgcccg ggcggcctca gtgagcgagc gagcgcgcag agagggagtg     120
gccaactcca tcactagggg ttcctggagg ggtggagtcg tgacgtgaat tacgtcatag     180
ggttagggag gtcctgtatt agaggtcacg tgagtgtttt gcgacatttt gcgacaccat     240
gtggtcacgc tgggtattta agcccgagtg agcacgcagg gtctccattt tgaagcggga     300
ggtttgaacg cgcagccgcc atgccggggt tttacgagat tgtgattaag gtccccagcg     360

-continued

```
accttgacga gcatctgccc ggcatttctg acagctttgt gaactgggtg gccgagaagg       420
aatgggagtt gccgccagat tctgacatgg atctgaatct gattgagcag caccccctga       480
ccgtggccga gaagctgcag cgcgactttc tgacggaatg gcgccgtgtg agtaaggccc       540
cggaggccct tttctttgtg caatttgaga agggagagag ctacttccac atgcacgtgc       600
tcgtggaaac caccggggtg aaatccatgg ttttgggacg tttcctgagt cagattcgcg       660
aaaaactgat tcagagaatt taccgcggga tcgagccgac tttgccaaac tggttcgcgg       720
tcacaaagac cagaaatggc gccggaggcg ggaacaaggt ggtggatgag tgctacatcc       780
ccaattactt gctccccaaa acccagcctg agctccagtg ggcgtggact aatatggaac       840
agtatttaag cgcctgtttg aatctcacgg agcgtaaacg gttggtggcg cagcatctga       900
cgcacgtgtc gcagacgcag gagcagaaca aagagaatca gaatcccaat tctgatgcgc       960
cggtgatcag atcaaaaact tcagccaggt acatggagct ggtcgggtgg ctcgtggaca      1020 agggattac ctcggagaag cagtggatcc aggaggacca ggcctcatac atctccttca      1080
atgcggcctc caactcgcgg tcccaaatca aggctgcctt ggacaatgcg ggaaagatta      1140
tgagcctgac taaaaccgcc cccgactacc tggtgggcca gcagcccgtg gaggacattt      1200
ccagcaatcg gatttataaa attttggaac taaacgggta cgatcccaa tatgcggctt      1260 ccgtctttct gggatgggcc acgaaaaagt tcggcaagag gaacaccatc tggctgtttg      1320
ggcctgcaac taccgggaag accaacatcg cggaggccat agcccacact gtgcccttct      1380
acgggtgcgt aaactggacc aatgagaact ttcccttcaa cgactgtgtc gacaagatgg      1440
tgatctggtg ggaggagggg aagatgaccg ccaaggtcgt ggagtcggcc aaagccattc      1500
tcggaggaag caaggtgcgc gtggaccaga aatgcaagtc ctcggcccag atagacccga      1560
ctcccgtgat cgtcacctcc aacaccaaca tgtgcgccgt gattgacggg aactcaacga      1620
ccttcgaaca ccagcagccg ttgcaagacc ggatgttcaa atttgaactc acccgccgtc      1680
tggatcatga cttttgggaag gtcaccaagc aggaagtcaa agacttttttc cggtgggcaa      1740 aggatcacgt ggttgaggtg gagcatgaat tctacgtcaa aaagggtgga gccaagaaaa      1800
gacccgcccc cagtgacgca gatataagtg agcccaaacg ggtgcgcgag tcagttgcgc      1860
agccatcgac gtcagacgcg gaagcttcga tcaactacgc agacaggtac caaaacaaat      1920
gttctcgtca cgtgggcatg aatctgatgc tgtttccctg cagacaatgc gagagaatga      1980
atcagaattc aaatatctgc ttcactcacg gacagaaaga ctgtttagag tgctttcccg      2040
tgtcagaatc tcaacccgtt tctgtcgtca aaaaggcgta tcagaaactg tgctacattc      2100
atcatatcat gggaaaggtg ccagacgctt gcactgcctg cgatctggtc aatgtggatt      2160
tggatgactg catctttgaa caataaatga tttaaatcag gtatggctgc cgatggttat      2220
cttccagatt ggctcgagga cactctctct gaaggaataa gacagtggtg gaagctcaaa      2280
cctgccccac caccaccaaa gcccgcagag cggcataagg acgacagcag gggtcttgtg      2340
cttcctgggt acaagtacct cggaccccttc aacggactcg acaagggaga gccggtcaac      2400
gaggcagacg ccgcggccct cgagcacgac aaagcctacg accggcagct cgacagcgga      2460
gacaacccgt acctcaagta caaccacgcc gacgcggagt tcaggagcg ccttaaagaa       2520 gatacgtctt tgggggcaa cctcggacga gcagtcttcc aggcgaaaaa gagggttctt       2580
gaacctctgg gcctggttga ggaacctgtt aagacggctc cgggaaaaaa gaggccggta       2640
gagcactctc ctgtggagcc agactcctcc tcgggaaccg gaaaggcggg ccagcagcct       2700
gcaagaaaaa gattgaattt tggtcagact ggagacgcag actcagtacc tgacccccag       2760
```

```
cctctcggac agccaccagc agcccctct ggtctgggaa ctaatacgat ggctacaggc    2820
agtggcgcac caatggcaga caataacgag ggcgccgacg gagtgggtaa ttcctcggga    2880
aattggcatt gcgattccac atggatgggc gacagagtca tcaccaccag cacccgaacc    2940
tgggccctgc ccacctacaa caaccacctc tacaaacaaa tttccagcca atcaggagcc    3000
tcgaacgaca tcactacttt ggctacagc accccttggg ggtattttga cttcaacaga    3060
ttccactgcc acttttcacc acgtgactgg caaagactca tcaacaacaa ctggggattc    3120
cgacccaaga gactcaactt caagctcttt aacattcaag tcaaagaggt cacgcagaat    3180
gacggtacga cgacgattgc caataacctt accagcacgg ttcaggtgtt tactgactcg    3240
gagtaccagc tcccgtacgt cctcggctcg gcgcatcaag gatgcctccc gccgttccca    3300
gcagacgtct tcatggtgcc acagtatgga tacctcaccc tgaacaacgg gagtcaggca    3360
gtaggacgct cttcatttta ctgcctggag tactttcctt ctcagatgct gcgtaccgga    3420
aacaacttta ccttcagcta cacttttgag gacgttcctt tccacagcag ctacgctcac    3480
agccagagtc tggaccgtct catgaatcct ctcatcgacc agtacctgta ttacttgagc    3540
agaacaaaca ctccaagtgg aaccaccacg cagtcaaggc ttcagttttc tcaggccgga    3600
gcgagtgaca ttcgggacca gtctaggaac tggcttcctg accctgtta ccgccagcag    3660 cgagtatcaa agacatctgc ggataacaac aacagtgaat actcgtggac tggagctacc    3720
aagtaccacc tcaatggcag agactctctg gtgaatccgg gcccggccat ggcaagccac    3780
aaggacgatg aagaaaagtt ttttcctcag agcggggttc tcatctttgg gaagcaaggc    3840
tcagagaaaa caaatgtgga cattgaaaag gtcatgatta cagacgaaga ggaaatcagg    3900
acaaccaatc ccgtggctac ggagcagtat ggttctgtat ctaccaacct ccagagaggc    3960
aacagacaag cagctaccgc agatgtcaac acacaaggcg ttcttccagg catggtctgg    4020
caggacagag atgtgtacct tcaggggccc atctgggcaa agattccaca cacggacgga    4080
cattttcacc cctctcccct catgggtgga ttcggactta aacaccctcc tccacagatt    4140
ctcatcaaga cacccccggt acctgcgaat ccttcgacca ccttcagtgc ggcaaagttt    4200
gcttccttca tcacacagta ctccacggga caggtcagcg tggagatcga gtgggagctg    4260
cagaaggaaa acagcaaacg ctggaatccc gaaattcagt acacttccaa ctacaacaag    4320
tctgttaatg tggactttac tgtggacact aatggcgtgt attcagagcc tcgccccatt    4380
ggcaccagat acctgactcg taatctgtaa ttgcttgtta atcaataaac cgtttaattc    4440
gtttcagttg aactttggtc tctgcgtatt tctttcttat ctagtttcca tggctacgta    4500
gataagtagc atggcgggtt aatcattaac tacaaggaac ccctagtgat ggagttggcc    4560
actccctctc tgcgcgctcg ctcgctcact gaggccgggc gaccaaaggt cgcccgacgc    4620
ccgggctttg cccgggcggc ctcagtgagc gagcgagcgc gcagagaggg agtggccaa    4679
```

<210> SEQ ID NO 13
<211> LENGTH: 735
<212> TYPE: PRT
<213> ORGANISM: adeno-associated virus 2 VP1 caspid protien

<400> SEQUENCE: 13

```
Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro
            20                  25                  30
```

-continued

```
Lys Pro Ala Glu Arg His Lys Asp Asp Ser Arg Gly Leu Val Leu Pro
        35                  40                  45
Gly Tyr Lys Tyr Leu Gly Pro Phe Asn Gly Leu Asp Lys Gly Glu Pro
        50                  55                  60
Val Asn Glu Ala Asp Ala Ala Leu Glu His Asp Lys Ala Tyr Asp
65                  70                  75                  80
Arg Gln Leu Asp Ser Gly Asp Asn Pro Tyr Leu Lys Tyr Asn His Ala
                85                  90                  95
Asp Ala Glu Phe Gln Glu Arg Leu Lys Glu Asp Thr Ser Phe Gly Gly
                100                 105                 110
Asn Leu Gly Arg Ala Val Phe Gln Ala Lys Lys Arg Val Leu Glu Pro
            115                 120                 125
Leu Gly Leu Val Glu Glu Pro Val Lys Thr Ala Pro Gly Lys Lys Arg
        130                 135                 140
Pro Val Glu His Ser Pro Val Glu Pro Asp Ser Ser Gly Thr Gly
145                 150                 155                 160
Lys Ala Gly Gln Gln Pro Ala Arg Lys Arg Leu Asn Phe Gly Gln Thr
                165                 170                 175
Gly Asp Ala Asp Ser Val Pro Asp Pro Gln Pro Leu Gly Gln Pro Pro
            180                 185                 190
Ala Ala Pro Ser Gly Leu Gly Thr Asn Thr Met Ala Thr Gly Ser Gly
        195                 200                 205
Ala Pro Met Ala Asp Asn Asn Glu Gly Ala Asp Gly Val Gly Asn Ser
    210                 215                 220
Ser Gly Asn Trp His Cys Asp Ser Thr Trp Met Gly Asp Arg Val Ile
225                 230                 235                 240
Thr Thr Ser Thr Arg Thr Trp Ala Leu Pro Thr Tyr Asn Asn His Leu
                245                 250                 255
Tyr Lys Gln Ile Ser Ser Gln Ser Gly Ala Ser Asn Asp Asn His Tyr
            260                 265                 270
Phe Gly Tyr Ser Thr Pro Trp Gly Tyr Phe Asp Phe Asn Arg Phe His
        275                 280                 285
Cys His Phe Ser Pro Arg Asp Trp Gln Arg Leu Ile Asn Asn Asn Trp
    290                 295                 300
Gly Phe Arg Pro Lys Arg Leu Asn Phe Lys Leu Phe Asn Ile Gln Val
305                 310                 315                 320
Lys Glu Val Thr Gln Asn Asp Gly Thr Thr Thr Ile Ala Asn Asn Leu
                325                 330                 335
Thr Ser Thr Val Gln Val Phe Thr Asp Ser Glu Tyr Gln Leu Pro Tyr
            340                 345                 350
Val Leu Gly Ser Ala His Gln Gly Cys Leu Pro Pro Phe Pro Ala Asp
        355                 360                 365
Val Phe Met Val Pro Gln Tyr Gly Tyr Leu Thr Leu Asn Asn Gly Ser
    370                 375                 380
Gln Ala Val Gly Arg Ser Ser Phe Tyr Cys Leu Glu Tyr Phe Pro Ser
385                 390                 395                 400
Gln Met Leu Arg Thr Gly Asn Asn Phe Thr Phe Ser Tyr Thr Phe Glu
                405                 410                 415
Asp Val Pro Phe His Ser Ser Tyr Ala His Ser Gln Ser Leu Asp Arg
            420                 425                 430
Leu Met Asn Pro Leu Ile Asp Gln Tyr Leu Tyr Tyr Leu Ser Arg Thr
        435                 440                 445
Asn Thr Pro Ser Gly Thr Thr Thr Gln Ser Arg Leu Gln Phe Ser Gln
```

-continued

```
            450                 455                 460
Ala Gly Ala Ser Asp Ile Arg Asp Gln Ser Arg Asn Trp Leu Pro Gly
465                 470                 475                 480

Pro Cys Tyr Arg Gln Gln Arg Val Ser Lys Thr Ser Ala Asp Asn Asn
                485                 490                 495

Asn Ser Glu Tyr Ser Trp Thr Gly Ala Thr Lys Tyr His Leu Asn Gly
            500                 505                 510

Arg Asp Ser Leu Val Asn Pro Gly Pro Ala Met Ala Ser His Lys Asp
            515                 520                 525

Asp Glu Glu Lys Phe Phe Pro Gln Ser Gly Val Leu Ile Phe Gly Lys
530                 535                 540

Gln Gly Ser Glu Lys Thr Asn Val Asp Ile Glu Lys Val Met Ile Thr
545                 550                 555                 560

Asp Glu Glu Glu Ile Arg Thr Thr Asn Pro Val Ala Thr Glu Gln Tyr
                565                 570                 575

Gly Ser Val Ser Thr Asn Leu Gln Arg Gly Asn Arg Gln Ala Ala Thr
            580                 585                 590

Ala Asp Val Asn Thr Gln Gly Val Leu Pro Gly Met Val Trp Gln Asp
            595                 600                 605

Arg Asp Val Tyr Leu Gln Gly Pro Ile Trp Ala Lys Ile Pro His Thr
    610                 615                 620

Asp Gly His Phe His Pro Ser Pro Leu Met Gly Gly Phe Gly Leu Lys
625                 630                 635                 640

His Pro Pro Pro Gln Ile Leu Ile Lys Asn Thr Pro Val Pro Ala Asn
                645                 650                 655

Pro Ser Thr Thr Phe Ser Ala Ala Lys Phe Ala Ser Phe Ile Thr Gln
                660                 665                 670

Tyr Ser Thr Gly Gln Val Ser Val Glu Ile Glu Trp Glu Leu Gln Lys
            675                 680                 685

Glu Asn Ser Lys Arg Trp Asn Pro Glu Ile Gln Tyr Thr Ser Asn Tyr
690                 695                 700

Asn Lys Ser Val Asn Val Asp Phe Thr Val Asp Thr Asn Gly Val Tyr
705                 710                 715                 720

Ser Glu Pro Arg Pro Ile Gly Thr Arg Tyr Leu Thr Arg Asn Leu
                725                 730                 735

<210> SEQ ID NO 14
<211> LENGTH: 598
<212> TYPE: PRT
<213> ORGANISM: adeno-associated virus 2 VP2 capsid protien

<400> SEQUENCE: 14

Met Ala Pro Gly Lys Lys Arg Pro Val Glu His Ser Pro Val Glu Pro
1               5                   10                  15

Asp Ser Ser Ser Gly Thr Gly Lys Ala Gly Gln Gln Pro Ala Arg Lys
            20                  25                  30

Arg Leu Asn Phe Gly Gln Thr Gly Asp Ala Asp Ser Val Pro Asp Pro
        35                  40                  45

Gln Pro Leu Gly Gln Pro Pro Ala Ala Pro Ser Gly Leu Gly Thr Asn
    50                  55                  60

Thr Met Ala Thr Gly Ser Gly Ala Pro Met Ala Asp Asn Asn Glu Gly
65                  70                  75                  80

Ala Asp Gly Val Gly Asn Ser Ser Gly Asn Trp His Cys Asp Ser Thr
                85                  90                  95
```

```
Trp Met Gly Asp Arg Val Ile Thr Thr Ser Thr Arg Thr Trp Ala Leu
        100                 105                 110

Pro Thr Tyr Asn Asn His Leu Tyr Lys Gln Ile Ser Gln Ser Gly
        115                 120                 125

Ala Ser Asn Asp Asn His Tyr Phe Gly Tyr Ser Thr Pro Trp Gly Tyr
    130                 135                 140

Phe Asp Phe Asn Arg Phe His Cys His Phe Ser Pro Arg Asp Trp Gln
145                 150                 155                 160

Arg Leu Ile Asn Asn Asn Trp Gly Phe Arg Pro Lys Arg Leu Asn Phe
                165                 170                 175

Lys Leu Phe Asn Ile Gln Val Lys Glu Val Thr Gln Asn Asp Gly Thr
            180                 185                 190

Thr Thr Ile Ala Asn Asn Leu Thr Ser Thr Val Gln Val Phe Thr Asp
        195                 200                 205

Ser Glu Tyr Gln Leu Pro Tyr Val Leu Gly Ser Ala His Gln Gly Cys
    210                 215                 220

Leu Pro Pro Phe Pro Ala Asp Val Phe Met Val Pro Gln Tyr Gly Tyr
225                 230                 235                 240

Leu Thr Leu Asn Asn Gly Ser Gln Ala Val Gly Arg Ser Ser Phe Tyr
                245                 250                 255

Cys Leu Glu Tyr Phe Pro Ser Gln Met Leu Arg Thr Gly Asn Asn Phe
            260                 265                 270

Thr Phe Ser Tyr Thr Phe Glu Asp Val Pro Phe His Ser Ser Tyr Ala
        275                 280                 285

His Ser Gln Ser Leu Asp Arg Leu Met Asn Pro Leu Ile Asp Gln Tyr
    290                 295                 300

Leu Tyr Tyr Leu Ser Arg Thr Asn Thr Pro Ser Gly Thr Thr Thr Gln
305                 310                 315                 320

Ser Arg Leu Gln Phe Ser Gln Ala Gly Ala Ser Asp Ile Arg Asp Gln
                325                 330                 335

Ser Arg Asn Trp Leu Pro Gly Pro Cys Tyr Arg Gln Gln Arg Val Ser
            340                 345                 350

Lys Thr Ser Ala Asp Asn Asn Asn Ser Glu Tyr Ser Trp Thr Gly Ala
        355                 360                 365

Thr Lys Tyr His Leu Asn Gly Arg Asp Ser Leu Val Asn Pro Gly Pro
    370                 375                 380

Ala Met Ala Ser His Lys Asp Asp Glu Glu Lys Phe Phe Pro Gln Ser
385                 390                 395                 400

Gly Val Leu Ile Phe Gly Lys Gln Gly Ser Glu Lys Thr Asn Val Asp
                405                 410                 415

Ile Glu Lys Val Met Ile Thr Asp Glu Glu Ile Arg Thr Thr Asn
            420                 425                 430

Pro Val Ala Thr Glu Gln Tyr Gly Ser Val Ser Thr Asn Leu Gln Arg
        435                 440                 445

Gly Asn Arg Gln Ala Ala Thr Ala Asp Val Asn Thr Gln Gly Val Leu
    450                 455                 460

Pro Gly Met Val Trp Gln Asp Arg Asp Val Tyr Leu Gln Gly Pro Ile
465                 470                 475                 480

Trp Ala Lys Ile Pro His Thr Asp Gly His Phe His Pro Ser Pro Leu
                485                 490                 495

Met Gly Gly Phe Gly Leu Lys His Pro Pro Pro Gln Ile Leu Ile Lys
            500                 505                 510

Asn Thr Pro Val Pro Ala Asn Pro Ser Thr Thr Phe Ser Ala Ala Lys
```

```
                515                 520                 525
Phe Ala Ser Phe Ile Thr Gln Tyr Ser Thr Gly Gln Val Ser Val Glu
            530                 535                 540
Ile Glu Trp Glu Leu Gln Lys Glu Asn Ser Lys Arg Trp Asn Pro Glu
545                 550                 555                 560
Ile Gln Tyr Thr Ser Asn Tyr Asn Lys Ser Val Asn Val Asp Phe Thr
                565                 570                 575
Val Asp Thr Asn Gly Val Tyr Ser Glu Pro Arg Pro Ile Gly Thr Arg
            580                 585                 590
Tyr Leu Thr Arg Asn Leu
        595

<210> SEQ ID NO 15
<211> LENGTH: 533
<212> TYPE: PRT
<213> ORGANISM: adeno-associated virus 2 VP3 capsid protien

<400> SEQUENCE: 15

Met Ala Thr Gly Ser Gly Ala Pro Met Ala Asp Asn Asn Glu Gly Ala
1               5                   10                  15
Asp Gly Val Gly Asn Ser Ser Gly Asn Trp His Cys Asp Ser Thr Trp
            20                  25                  30
Met Gly Asp Arg Val Ile Thr Thr Ser Thr Arg Thr Trp Ala Leu Pro
        35                  40                  45
Thr Tyr Asn Asn His Leu Tyr Lys Gln Ile Ser Ser Gln Ser Gly Ala
    50                  55                  60
Ser Asn Asp Asn His Tyr Phe Gly Tyr Ser Thr Pro Trp Gly Tyr Phe
65                  70                  75                  80
Asp Phe Asn Arg Phe His Cys His Phe Ser Pro Arg Asp Trp Gln Arg
                85                  90                  95
Leu Ile Asn Asn Asn Trp Gly Phe Arg Pro Lys Arg Leu Asn Phe Lys
            100                 105                 110
Leu Phe Asn Ile Gln Val Lys Glu Val Thr Gln Asn Asp Gly Thr Thr
        115                 120                 125
Thr Ile Ala Asn Asn Leu Thr Ser Thr Val Gln Val Phe Thr Asp Ser
    130                 135                 140
Glu Tyr Gln Leu Pro Tyr Val Leu Gly Ser Ala His Gln Gly Cys Leu
145                 150                 155                 160
Pro Pro Phe Pro Ala Asp Val Phe Met Val Pro Gln Tyr Gly Tyr Leu
                165                 170                 175
Thr Leu Asn Asn Gly Ser Gln Ala Val Gly Arg Ser Ser Phe Tyr Cys
            180                 185                 190
Leu Glu Tyr Phe Pro Ser Gln Met Leu Arg Thr Gly Asn Asn Phe Thr
        195                 200                 205
Phe Ser Tyr Thr Phe Glu Asp Val Pro Phe His Ser Ser Tyr Ala His
    210                 215                 220
Ser Gln Ser Leu Asp Arg Leu Met Asn Pro Leu Ile Asp Gln Tyr Leu
225                 230                 235                 240
Tyr Tyr Leu Ser Arg Thr Asn Thr Pro Ser Gly Thr Thr Thr Gln Ser
                245                 250                 255
Arg Leu Gln Phe Ser Gln Ala Gly Ala Ser Asp Ile Arg Asp Gln Ser
            260                 265                 270
Arg Asn Trp Leu Pro Gly Pro Cys Tyr Arg Gln Gln Arg Val Ser Lys
        275                 280                 285
```

```
Thr Ser Ala Asp Asn Asn Ser Glu Tyr Ser Trp Thr Gly Ala Thr
    290                 295                 300
Lys Tyr His Leu Asn Gly Arg Asp Ser Leu Val Asn Pro Gly Pro Ala
305                 310                 315                 320
Met Ala Ser His Lys Asp Asp Glu Glu Lys Phe Phe Pro Gln Ser Gly
                325                 330                 335
Val Leu Ile Phe Gly Lys Gln Gly Ser Glu Lys Thr Asn Val Asp Ile
            340                 345                 350
Glu Lys Val Met Ile Thr Asp Glu Glu Ile Arg Thr Thr Asn Pro
    355                 360                 365
Val Ala Thr Glu Gln Tyr Gly Ser Val Ser Thr Asn Leu Gln Arg Gly
    370                 375                 380
Asn Arg Gln Ala Ala Thr Ala Asp Val Asn Thr Gln Gly Val Leu Pro
385                 390                 395                 400
Gly Met Val Trp Gln Asp Arg Asp Val Tyr Leu Gln Gly Pro Ile Trp
                405                 410                 415
Ala Lys Ile Pro His Thr Asp Gly His Phe His Pro Ser Pro Leu Met
                420                 425                 430
Gly Gly Phe Gly Leu Lys His Pro Pro Pro Gln Ile Leu Ile Lys Asn
            435                 440                 445
Thr Pro Val Pro Ala Asn Pro Ser Thr Thr Phe Ser Ala Ala Lys Phe
    450                 455                 460
Ala Ser Phe Ile Thr Gln Tyr Ser Thr Gly Gln Val Ser Val Glu Ile
465                 470                 475                 480
Glu Trp Glu Leu Gln Lys Glu Asn Ser Lys Arg Trp Asn Pro Glu Ile
                485                 490                 495
Gln Tyr Thr Ser Asn Tyr Asn Lys Ser Val Asn Val Asp Phe Thr Val
            500                 505                 510
Asp Thr Asn Gly Val Tyr Ser Glu Pro Arg Pro Ile Gly Thr Arg Tyr
            515                 520                 525
Leu Thr Arg Asn Leu
    530

<210> SEQ ID NO 16
<211> LENGTH: 6
<212> TYPE: PRT
<213> ORGANISM: Artificial Sequence
<220> FEATURE:
<223> OTHER INFORMATION: Bovine Papilloma Virus peptide

<400> SEQUENCE: 16

Thr Pro Phe Tyr Leu Lys
1               5

<210> SEQ ID NO 17
<211> LENGTH: 10
<212> TYPE: PRT
<213> ORGANISM: Artificial Sequence
<220> FEATURE:
<223> OTHER INFORMATION: Luteinizing Hormone peptide

<400> SEQUENCE: 17

His Cys Ser Thr Cys Tyr Tyr His Lys Ser
1               5                   10

<210> SEQ ID NO 18
<211> LENGTH: 5
<212> TYPE: PRT
<213> ORGANISM: Artificial Sequence
```

```
-continued

<220> FEATURE:
<223> OTHER INFORMATION: synthetic targeting peptide

<400> SEQUENCE: 18

Phe Val Phe Lys Pro
1               5
```

AAV2 VECTORS AND METHODS

RELATED APPLICATIONS

The present application claims priority benefit of U.S. Provisional Application No. 60/260,124 filed Jan. 5, 2001 which is herein incorporated by reference in its entirety.

FIELD OF THE INVENTION

The invention relates to Adeno-associated virus vectors. In particular, it relates to Adeno-associated virus vectors with modified capsid proteins and materials and methods for their preparation and use.

BACKGROUND

Adeno-associated virus (AAV) is a replication-deficient parvovirus, the single-stranded DNA genome of which is about 4.7 kb in length including 145 nucleotide inverted terminal repeat (ITRs). The nucleotide sequence of the AAV serotype 2 (AAV2) genome is presented in Srivastava et al., *J. Virol.,* 45: 555–564 (1983) as corrected by Ruffing et al., *J. Gen. Virol.,* 75: 3385–3392 (1994) Cis-acting sequences directing viral DNA replication (rep), encapsidation/packaging and host cell chromosome integration are contained within the ITRs. Three AAV promoters, p5, p19, and p40 (named for their relative map locations), drive the expression of the two AAV internal open reading frames encoding rep and cap genes. The two rep promoters (p5 and p19), coupled with the differential splicing of the single AAV intron (at nucleotides 2107 and 2227), result in the production of four rep proteins (rep 78, rep 68, rep 52, and rep 40)from the rep gene. Rep proteins possess multiple enzymatic properties which are ultimately responsible for replicating the viral genome. The cap gene is expressed from the p40 promoter and it encodes the three capsid proteins VP1, VP2, and VP3. Alternative splicing and non-consensus translational start sites are responsible for the production of the three related capsid proteins. A single consensus polyadenylation site is located at map position 95 of the AAV genome. The life cycle and genetics of AAV are reviewed in Muzyczka, *Current Topics in Microbiology and Immunology,* 158: 97–129 (1992).

When AAV infects a human cell, the viral genome can integrate into chromosome 19 resulting in latent infection of the cell. Production of infectious virus does not occur unless the cell is infected with a helper virus (for example, adenovirus or herpesvirus). In the case of adenovirus, genes E1A, E1B, E2A, E4 and VA provide helper functions. Upon infection with a helper virus, the AAV provirus is rescued and amplified, and both AAV and adenovirus are produced.

AAV possesses unique features that make it attractive as a vaccine vector for expressing immunogenic peptides/polypeptides and as a vector for delivering foreign DNA to cells, for example, in gene therapy. AAV infection of cells in culture is noncytopathic, and natural infection of humans and other animals is silent and asymptomatic Moreover, AAV infects many mammalian cells allowing the possibility of targeting many different tissues in vivo. Replication of the viral DNA is not required for integration, and thus helper virus is not required for this process. The AAV proviral genome is infectious as cloned DNA in plasmids which makes construction of recombinant genomes feasible. Furthermore, because the signals directing AAV replication, genome encapsidation and integration are contained within the ITRs of the AAV genome, some or all of the internal approximately 4.3 kb of the genome (encoding replication and structural capsid proteins, rep-cap) may be replaced with foreign DNA such as a gene cassette containing a promoter, a DNA of interest and a polyadenylation signal. The rep and cap proteins may be provided in trans. Another significant feature of AAV is that it is an extremely stable and hearty virus. It easily withstands the conditions used to inactivate adenovirus (56° to 65° C. for several hours), making cold preservation of rAAV-vectors less critical. AAV may even be lyophilized. Finally, AAV-infected cells are not resistant to superinfection.

Recent research on AAV has therefore involved attempts to modify the viral genome. As the range of cells that AAV will infect is so broad, some researches have focused on modifying the virus so that it targets specific types of cells for infection. The cellular range or tropism of the virus is determined by the binding of AAV capsid protein(s) to receptor and/or coreceptor proteins expressed on the surface of target cells. Heparin-sulfate proteoglycan (HSPG) is the primary cellular attachment receptor for AAV2. In attempts to enable AAV to bind other cellular receptors, mutagenesis of the AAV capsid-encoding DNA to encode heterologous targeting peptides as part of a capsid protein has produced varying results. For example, Girod et al. (*Nature Medicine,* 5: 1052–1056, 1999) describes AAV2 insertional mutants generated to target L14-specific integrin receptors. These mutant AAV2 vectors expressed capsid proteins which had a fourteen amino acid peptide comprising the RGD domain of the laminin fragment P1 inserted at six different sites. Rabinowitz et al. (*Virology,* 265: 274–285, 1999) attempted to identify capsid domains and positions which were capable of tolerating insertions without loss of function. Related PCT application WO 00/28004 describes the modified capsid proteins containing insertions such as melanocyte stimulating hormone, poly-histidine tracts, poly-lysine tracts, an RGD domain and bradykinin. Only a few of the modified capsid proteins could be incorporated into functional viral particles and titers of the viruses were drastically lower than wild-type virus.

SUMMARY OF THE INVENTION

The present inventors recognized a need in the art for identification of sites in the AAV capsid protein(s) from which peptides/polypeptides of interest may be presented in a desired conformation to allow the development of AAV vectors that deliver DNA to specific target cells and the development of AAV vectors that present/display on their surface immunogenic peptides/polypeptides. The invention is based on the elucidation of sites/regions in the AAV2 capsid protein that are amenable to insertion of heterologous peptides, the development of scaffolding sequences required for proper conformation of peptides, and the construction of AAV2 vectors with altered tropism. The full length nucleotide sequence of the wild type AAV2 vector is set out as SEQ ID NO: 12. The amino acid sequence of VP1 capsid protein (SEQ ID NO: 13) is encoded by the nucleotides 2203–4410 of SEQ ID NO: 12, the amino acid sequence of VP2 capsid protein (SEQ ID NO: 14) is encoded by nucleotides 2614–4410 of SEQ ID NO: 12 and the amino acid sequence of VP3 capsid protein (SEQ ID NO: 15) is encoded by nucleotides 2809–4410 of SEQ ID NO: 12.

The present invention provides AAV vectors (viral particles) encoding capsid proteins that comprise insertions of amino acids of interest (i.e., peptides or polypeptides). Preferably, the AAV vectors are AAV2 vectors. Also preferably, DNA encoding the insertions follows the cap gene DNA encoding amino acid position 139 and/or position 161 in the VP1/VP2 capsid region, and/or amino acid position 459, 584, 588 and/or 657 in the VP3 region. While the capsid sites/regions amenable to insertions have been described herein with respect to AAV2, those skilled in the art will understand that corresponding sites in other parvoviruses, both autonomously-replicating parvoviruses and other AAV dependent viruses, are also sites/regions amenable to insertions in those viruses. The amino acids of interest may impart a different binding/targeting ability to the vector or may themselves be immunogenic. As a result, the vectors of the invention exhibit altered characteristics in comparison to wild type AAV, including but not limited to, altered cellular tropism and/or antigenic properties. The invention also contemplates cells, plasmids and viruses which comprise polynucleotides encoding the capsid proteins of the invention.

It is contemplated that in addition to amino acids of interest, amino acids serving as linker/scaffolding sequences as described herein may be included in the AAV vector capsid insert to maintain the functional conformation of the capsid. The linker/scaffolding sequences are short sequences which flank the insertion of interest in the mutated capsid protein. For example, the insertion may have the amino acids TG at its amino terminus and the tripeptide ALS, GLS or LLA at its carboxy terminus.

Techniques to produce AAV vectors, in which a AAV genome to be packaged, rep and cap genes, and helper virus functions are provided to a cell are standard in the art. Production of AAV vectors requires that the following components are present within a single cell (denoted herein as a packaging cell): a rAAV construct consisting of a DNA of interest flanked by AAV inverted terminal repeats, an AAV helper construct containing the capsid gene (which may or may not be comprise an insert) and the rep gene, and an adenovirus helper plasmid or infected with an adenovirus. The rAAV construct may be delivered to a packaging cell by transfection in a plasmid, infection by a viral genome or may be integrated into the packaging cell genome. The AAV helper construct may be delivered to a packaging cell by transfection of a plasmid or integrated into the packaging cell genome. The adenovirus helper plasmid or adenovirus may be delivered to the packaging cell by transfection/infection. The term "helper virus functions" refers to the functions carried out by the addition of an adenovirus helper plasmid or infection of adenovirus to support production of AAV viral particles.

One method generating a packaging cell with all the necessary components for AAV production is the triple transfection method. In this method a cell such as a 293 cell is transfected with the rAAV construct, the AAV helper construct and a adenovirus helper plasmid or infected with adenovirus. The advantages of the triple transfection method are that it is easily adaptable and straightforward. Generally, this method is used for small scale vector preparations.

Another method of generating a packaging cell is to create a cell line which stably expresses all the necessary components for AAV vector production. For example, a plasmid expressing the rAAV construct, a helper construct expressing the rep and cap proteins (modified or wild type) and a selectable marker, such as Neo, are integrated into the genome of a cell. The packaging cell line is then infected with a helper virus such as adenovirus. The advantages of this method are that the cells are selectable and are suitable for large-scale production of the vector.

In another aspect the invention provides AAV helper constructs encoding a AAV cap gene comprising DNA encoding an insertion of one or more amino acids in the encoded capsid protein(s). The insertion is at a position of the encoded capsid protein(s) that is exposed on the surface of an AAV vector comprising the capsid protein(s) and that does not disrupt conformation of the capsid protein(s) in a manner that prevents assembly of the vector or infectivity of the vector. Limited by these criteria, the size of the insert may vary from as short as two amino acids to as long as amino acids encoding an entire protein. Also provided are cells that stably or transiently produce AAV vectors of the invention. Methods of producing AAV vectors using such cells are contemplated by the invention.

In one embodiment, the AAV vectors of the invention comprising capsid proteins with binding/targeting amino acids inserted are useful for the therapeutic delivery and/or transfer of nucleic acids to animal (including human) cells both in vitro and in vivo. Nucleic acids of interest include nucleic acids encoding peptides and polypeptides, such as therapeutic (e.g., for medical or veterinary uses) peptides or polypeptides. A therapeutic peptide or polypeptide is one that may prevent or reduce symptoms that result from an absence or defect in a protein in a cell or person. Alternatively, a therapeutic peptide or polypeptide is one that otherwise confers a benefit to a subject, e.g., anti-cancer effects. As a further alternative, the nucleic acid may encode a reporter peptide or protein (e.g., an enzyme). In yet still another alternative, the nucleic acid of interest may be an antisense nucleic acid or a ribozyme.

In another embodiment, the AAV vectors are useful as vaccines. The use of parvoviruses as vaccines is known in the art. Immunogenic amino acids (peptides or polypeptides) may be presented as inserts in the AAV vector capsid. Alternatively, immunogenic amino acids may be expressed from a heterologous nucleic acid introduced into a recombinant AAV genome and carried by the AAV vector. If the immunogenic amino acids are expressed from a recombinant AAV genome, the AAV vector of the invention preferably exhibits an altered cellular tropism and comprises a capsid protein with an insertion of targeting amino acids that are different from those of wild type AAV. Immunogenic amino acids may be from any source (e.g., bacterial, viral or tumor antigens).

AAV vectors of the invention that exhibit an altered cellular tropism may differ from wild type in that the natural tropism of AAV may be reduced or abolished by insertion or substitution of amino acids of interest in a capsid protein of the vector. Alternatively, the insertion or substitution of the amino acids may target the vector to a particular cell type(s) perhaps not targeted by wild type AAV. Cell types of interest contemplated by the invention include, for example, glial cells, airway epithelium cells, hematopoietic progenitors cells and tumor cells. In preferred embodiments, capsid amino acids are modified to remove wild type tropism and to introduce a new tropism. The inserted or substituted amino acid may comprise targeting peptides and polypeptides that are ligands and other peptides that bind to cell surface receptors and glycoproteins as well as fragments thereof that retain the ability to target vectors to cells. The targeting peptide or polypeptide may be any type of antibody or antigen-binding fragment thereof that recognizes, e.g., a cell-surface epitope. The binding domain from a toxin can be used to target the AAV vector to particular target cells of interest. It is also contemplated that AAV vectors of the invention may be targeted to a cell using a "nonclassical" import/export signal peptide (e.g., fibroblast growth factor-1 and -2, interleukin 1, HIV-1 Tat protein, herpes virus VP22 protein, and the like).

Also contemplated as targeting peptides are peptides that direct uptake of the AAV vector by specific cells. For example, a FVFLP peptide (SEQ ID NO: 18) triggers uptake by liver cells. Another peptide contemplated to direct uptake by cancer cells is the RGD peptide, e.g., 4C-RGD. The RGD domain is known to mediate interactions between extracelluar matrix proteins and integrin receptors located on the surface of cancer cells. It is contemplated that the insertion of an RGD peptide into the capsid of the AAV vector will act as a cell entry mechanism specific to cancer cells. The receptor-binding peptide from luteinizing hormone is also contemplated as a peptide which when inserted into the capsid of an AAV vector will direct entry into ovarian cells since ovarian cells express luteinizing hormone receptors.

Other targeting peptide contemplated influence cellular trafficking of viral particles. Phage display techniques, as well as other techniques known in the art, may be used to identify peptides that recognize, preferably specifically, a cell type of interest. Alternatively, the targeting sequence comprises amino acids that may be used for chemical coupling (e.g., through amino acid side groups of arginine or lysine residues) of the capsid to another molecule that directs entry of the AAV vector into a cell.

The present invention also encompasses modified AAV vectors, the capsid protein(s) of which are biotinylated in vivo. For example, the invention contemplates AAV capsids engineered to include the biotin acceptor peptide (BAP). Expression of the *E. coli* enzyme biotin protein ligase during AAV vector biosynthesis in the presence of biotin results in biotinylation of the AAV capsid proteins as they are made and assembled into viral particles.

In order to biotinylate the AAV viral particles, a system for expressing the biotin ligase enzyme in packaging cell lines is contemplated by the present invention. The invention provides for plasmids, such as the pCMV plasmid, which direct expression of the biotin ligase gene within the packaging cell line. For production of the biotinylated AAV vector the following components need to be transfected into a packaging cell: a rAAV vector comprising DNA of interest flanked by AAV inverted terminal repeats, an AAV helper construct containing a capsid gene with a BAP insert and the rep gene, adenovirus helper plasmid or infected with adenovirus, and the biotin ligase gene (BirA). In this system, the biotin ligase gene may be expressed by a plasmid including the BirA gene (such as pCMV-BirA) infection with an adenovirus which expresses the BirA gene or by using a packaging cell line that is stably transfected with the BirA gene.

It is contemplated that the biotinylated AAV viral particles will serve as substrates for conjugation of targeting motifs (e.g., monoclonal antibodies, growth factors, cytokines) to the surface of vector particles through utilizing avidin/strepavidin-biotin chemistry. In addition, the biotinylated AAV viral particles are contemplated to be useful for visualizing the biodistribution of the viral particles both in vivo and in vitro. The biotinylated viral particles can be visualized with fluorescence or enzymatically with labeled strepavidin compounds. Biotinylation is also useful for conjugating epitope shielding moieties, such as polyethylene glycol, to the AAV vector. The conjugation of shielding moieties allows the vector to evade immune recognition. Biotinylation of the AAV vector is also contemplated to enhance intracellular trafficking of viral particles through conjugation of proteins or peptides such as nuclear transport proteins. Biotinylation may also be used to conjugate proteins or peptides which affect the processing of AAV vector genomes such as increasing the efficiency of integration. In addition, biotinylation may also be used to conjugate proteins or peptides that affect the target cells, e.g., proteins that make a target cell more susceptible to infection or proteins that activate a target cell thereby making it a better target for the expression of a therapeutic or antigenic peptide.

The present invention also provides compositions comprising an AAV vector of the invention in a pharmaceutically acceptable carrier. The compositions may also comprise other ingredients such as diluents and adjuvants. Acceptable carriers, diluents and adjuvants are nontoxic to recipients and are preferably inert at the dosages and concentrations employed, and include buffers such as phosphate, citrate, or other organic acids; antioxidants such as ascorbic acid; low molecular weight polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as Tween, pluronics or polyethylene glycol (PEG).

Methods of eliciting an immune response to amino acids of interest are contemplated by the invention. The methods comprise a step of administering an immunogenic dose of a composition comprising a AAV vector of the invention to a animal (including a human person) in need thereof. In the methods, the immunogenic amino acids may be inserted in the AAV vector capsid protein(s) or may be encoded by a recombinant genome encapsidated as the AAV vector. An immunogenic dose of a composition of the invention is one that generates, after administration, a detectable humoral and/or cellular immune response in comparison to the immune response detectable before administration or in comparison to a standard immune response before administration. The invention contemplates that the immune response resulting from the methods may be protective and/or therapeutic.

Therapeutic methods of delivering and/or transferring nucleic acids of interest to a host cell are also contemplated by the invention. The methods comprise the step of administering a therapeutically effective dose of a composition comprising a AAV vector of the invention to an animal (including a human person) in need thereof. A therapeutically effective dose is a dose sufficient to alleviate (eliminate or reduce) at least one symptom associated with the disease state being treated. Administration of the therapeutically effective dose of the compositions may be by routes standard in the art, for example, parenteral, intravenous, oral, buccal, nasal, pulmonary, rectal, or vaginal.

Titers of AAV vector to be administered in methods of the invention will vary depending, for example, on the particular virus vector, the mode of administration, the treatment goal, the individual, and the cell type(s) being targeted, and may be determined by methods standard in the art.

DETAILED DESCRIPTION

The present invention is illustrated by the following examples that are not intended to limit the invention. Example I describes construction of AAV packaging plasmids encoding altered capsid proteins and analysis of the ability of the altered capsid proteins to be assembled into infectious AAV vectors. Example 2 presents assays for the surface expression of epitopes inserted in the altered capsid proteins. Example 3 describes experiments testing whether the AAV vectors retained HSPG-binding ability. Example 4 describes construction and characterization of a mutant AAV vector containing a double insertion within the capsid protein. Example 5 includes analysis of the effect of linker and scaffold sequences on the altered capsid proteins. Example 6 presents the results of experiments in which AAV vectors encoding capsid proteins with an insertion of an luteinizing hormone receptor binding peptide were able to transduce OVCAR-3 cells. Example 6 also discusses various indications amenable to use of AAV vectors of the invention. Example 7 and 8 describe fourteen additional modified AAV vectors, wherein the RGD-4C peptide motif was inserted into the capsid proteins. The experiments described in Example 9 demonstrate that the AAV-RGD vectors attach to and enter cells via integrin receptors. Example 10 demonstrates that the AAV-RGD vectors were capable of mediating gene delivery via integrin receptors. Example demonstrates that the AAV-RGD vectors transferred genes to ovarian adenocarcinoma cell lines. Example 12 describes AAV mediated eGFP gene delivery to human ovarian tumor xenografts established in SCID mice. Example 13 describes construction of mutant AAV vectors which are biotinylated in vivo through an insertion of the biotin acceptor peptide in the capsid protein. Finally, Example 14 describes a packaging system for biotinylated AAV vectors.

EXAMPLE 1

In order to identify sites within the AAV2 capsid that could tolerate insertion of targeting epitopes, an extensive site-specific mutagenesis strategy was designed. Regions of the AAV2 capsid DNA to be modified were chosen by analyzing data from a number of sources to predict which ones encoded capsid amino acids that were exposed on the surface of the virion and which encoded amino acids that could be replaced with other amino acids without significantly altering the conformation of the rest of the capsid protein(s). One source of data was a comparison of structural information from five related autonomous parvoviruses. The five parvoviruses had solved virion structures and included canine parvovirus (CPV) (Tsao et al., Science, 251: 1456–1464 and Wu et al., J. Mol. Biol, 233: 231–244), feline panleukopenia virus (FPV)(Agbandje et al., Proteins, 16: 155–171), minute virus of mice (MVM)(Agbandje-McKenna et al., Structure, 6: 1369–1381 and Llamas-Saiz et al., Acta Crystallogr. Sect. D. Biol. Crystallogr., 53: 93–102), parvovirus B19 (B19)(Chipman et al., Proc. Natl. Acad. Sci. USA, 93: 7502–7506) and Aleutian mink disease parvovirus (ADV)(McKenna et al., J. Virol., 73: 6882–6891). This information was compared to a computer-predicted secondary structure of the AAV2 capsid based on its known primary amino acid sequence. Other sources of data were previous reports of immunogenic regions of the AAV2 capsid and previous reports of effects of random capsid mutations. Finally, the AAV2 capsid primary amino acid sequence was compared with that of other AAV and other parvoviridae for regions of defined secondary structure to create a model of the AAV2 capsid. From the model sites for insertion of small peptides two to fifteen amino acids in length were chosen. A series of thirty-eight virus mutants containing peptide insertions at twenty-five unique sites within the AAV2 capsid protein was generated. Most of the insertions were within the VP1 capsid protein (19/25), four were within the VP1 unique region and two were within the VP1/VP2 unique region. Epitopes inserted within the VP3 protein are expected to be displayed on every capsid monomer within the AAV virion (60/virion). Insertions within the VP1 or VP1/VP2 unique regions would be expected to be displayed three and six times, respectively, per virion.

Site-directed mutagenesis was performed on plasmid pUC-Cap (a subclone of the AAV2 Rep and Cap open reading frames (ORF)). Mutagenesis was confirmed by restriction endonuclease digestion. The altered Cap genes were then substituted for the wild-type AAV2 sequences in plasmid pACG2 to generate the series of mutant helper plasmids described in Table 1 below, wherein epitope AgeI is the amino acids encoded by an AgeI restriction site, epitope NgoMI is the amino acids encoded by an NgoMI restriction site, epitope 4C-RGD is a cyclic RGD-based peptide (CDCRGDCFC; SEQ ID NO: 10) that has been shown to bind a number of integrins, including $\alpha_v\beta_3$, $\alpha_v\beta_5$, $\alpha_5\beta_1$, $\alpha_5\beta_1$, $\alpha_3\beta_1$, $\alpha_2\beta_1$ and $\alpha_6\beta_1$, present on the surface of mammalian cells that is useful for targeting to tumor endothelium and other cell types, epitope BPV is a peptide from bovine papilloma virus (TPPYLK; SEQ ID NO: 16), and epitope LH is a receptor-binding peptide from luteinizing hormone (HCSTCYYHKS; SEQ ID NO: 17). Plasmid nomenclature in the Table 1 can be understood by reference to plasmid pACG-A139 wherein pACG refers to the starting plasmid in which mutant cap sequences were inserted and A139 refers to insertion of an AgeI restriction site after position 139 of the capsid, and by reference to plasmid pACG-A139BPV/GLS wherein BPV indicates the peptide of interest that is inserted and /GLS indicates inclusion of linker amino acids at the carboxy terminus of the inserted epitope.

TABLE 1

Mutant AAV Packaging Plasmids

| Mutant Plasmid Designation | Location | Insertion (epitope) |
| --- | --- | --- |
| pACG-A26 | VP1 | TG (Age I) |
| pACG-A46 | VP1 | TG (Age I) |
| pACG-A115-4C-RGD/GLS | VP1 | TGCDCRGDCFCGLS (SEQ ID NO: 1) (4C-RGD) |
| pACG-A120 | VP1 | TG (Age I) |
| pACG-A139 | VP2 | TG (Age I) |
| pACG-A139BPV/GLS | VP2 | TGTPFYLKGLS (SEQ ID NO: 2) (BPV) |
| pACG-A139LH/GLS | VP2 | TGHCSTCYYHKSGLS (SEQ ID NO: 3) (LH) |
| pACG-A161BPV/ALS | VP2 | TGTPFYLKALS (SEQ ID NO: 4) (BPV) |
| pACG-A161BPV/LLA | VP2 | TGTPFYLKLLA (SEQ ID NO: 5) (BPV) |
| pACG-A161BPV/GLS | VP2 | TGTPFYLKGLS (SEQ ID NO: 2) (BPV) |
| pACG-A161LH/GLS | VP2 | TGHCSTCYYHKSGLS (SEQ ID NO: 3) (LH) |
| pACG-A312 | VP3 | TG (Age I) |
| pACG-N319 | VP3 | AG (NgoMI) |
| pACG-A323-4C-RGD/GLS | VP3 | TGCDCRGDCFCGLS (SEQ ID NO: 1) (4C-RGD) |
| pACG-A339BPV | VP3 | TGTPFYLK (SEQ ID NO: 6) (BPV |
| pACG-A375BPV | VP3 | TGTPFYLK (SEQ ID NO: 6) (BPV) |
| pACG-A441 | VP3 | TG (Age I) |
| pACG-A459 | VP3 | TG (Age I) |
| pACG-A459BPV/GLS | VP3 | TGTPFYLKGLS (SEQ ID NO: 2) (BPV) |
| pACG-A459LH/GLS | VP3 | TGHCSTCYYHKSGLS (SEQ IS NO: 3) (LH) |
| pACG-A466 | VP3 | TG (Age I) |
| pACG-A480-4C-RGD/GLS | VP3 | TGCDCRGDCFCGLS (SEQ ID NO: 1) (4C-RGD) |
| pACG-N496 | VP3 | AG (NgoMI) |
| pACG-A520LH/GLS | VP3 | TGHCSTCYYHKSGLS (SEQ ID NO: 3) (LH) |
| pACG-A520BPV/LLA | VP3 | TGTPFYLKLLA (SEQ ID NO: 5) (BPV) |
| pACG-A540 | VP3 | TG (Age I) |
| pACG-N549 | VP3 | AG (NgoMI) |

TABLE 1-continued

Mutant AAV Packaging Plasmids

| Mutant Plasmid Designation | Location | Insertion (epitope) |
|---|---|---|
| pACG-N584 | VP3 | AG (NgoMI) |
| pACG-A584BPV/ALS | VP3 | TGTPFYLKALS (SEQ ID NO: 4) (BPV) |
| pACG-A584BPV/LLA | VP3 | TGTPFYLKLLA (SEQ ID NO: 5) (BPV) |
| pACG-A584BPV/GLS | VP3 | TGTPFYLKGLS (SEQ ID NO: 2) (BPV) |
| pACG-N472 | VP3 | AG (NgoMI) |
| pACG-A587BPV/ALS | VP3 | TGTPFYLKALS (SEQ ID NO: 4) (BPV) |
| pACG-A587BPV/LLA | VP3 | TGTPFYLKLLA (SEQ ID NO: 5) (BPV) |
| pACG-A587BPV/GLS | VP3 | TGTPFYLKGLS (SEQ ID NO: 2) (BPV) |
| pACG-A595-4C-RGD/GLS | VP3 | TGCDCRGDCFCGLS (SEQ ID NO: 1) (4C-RGD) |
| pACG-A597-4C-RGD/GLS | VP3 | TGCDCRGDCFCGLS (SEQ ID NO: 1) (4C-RGD) |
| pACG-A657 | VP3 | TG (Age I) |

The mutant AAV packaging plasmids were tested for their ability to generate AAV vectors with altered capsids by triple transfection with plasmid pAAV-LacZ (a plasmid containing LacZ flanked by AAV ITRs) and pXX6-80 (a plasmid containing Adenovirus helper DNA) according to established procedures. AAV vector preparations were assessed for particle formation and vector infectivity. Particles were identified by ELISA using A20 monoclonal antibody, whereas DNA-containing particles were identified by dot-blot and/or PCR. Vector particles were tested for infectivity by cellular transduction assay on Adenovirus-infected C12 cells. Capsid mutants were grouped into three types. Capsid mutants that did not give rise to any viral particles were classified as Type I (7/38). Mutants that produced non-infectious particles were classified as Type II (11/38) and mutants that produced fully infectious viral particles were classified as Type III (20/38). See Table 2 below wherein the actual titers are listed as values for comparison with the wild type titer unless the titer (−) is four orders of magnitude or more less than wild type vector and a titer (+) is below the sensitivity of DNA dot blot but detectable by PCR.

TABLE 2

Mutant AAV Vector Characterization Particle titer

| Mutant Vector Designation | Dot-blot | A20 ELISA | Infections titer | Mutant Type |
|---|---|---|---|---|
| AAV-A26 | (+) | $7.5 \times 10^7$ | — | II |
| AAV-A46 | $9.2 \times 10^7$ | $8.0 \times 10^7$ | $1.2 \times 10^3$ | III |
| AAV-A115-4C-RGD/GLS | $5.6 \times 10^7$ | $7.5 \times 10^7$ | $1.2 \times 10^2$ | III |
| AAV-A120 | $3.4 \times 10^7$ | $8.0 \times 10^7$ | $1.0 \times 10^3$ | III |
| AAV-A139 | $2.0 \times 10^7$ | $9.0 \times 10^7$ | $5.0 \times 10^5$ | III |
| AAV-A139BPV/GLS | $1.4 \times 10^8$ | $9.0 \times 10^7$ | $6.8 \times 10^5$ | III |
| AAV-A139LH/GLS | $1.2 \times 10^8$ | $8.0 \times 10^7$ | $3.3 \times 10^5$ | III |
| AAV-A161BPV/ALS | $4.0 \times 10^7$ | $8.0 \times 10^7$ | $1.2 \times 10^5$ | III |
| AAV-A161BPV/LLA | $1.4 \times 10^6$ | $7.5 \times 10^5$ | $5.9 \times 10^2$ | III |
| AAV-A161BPV/GLS | $1.2 \times 10^7$ | $7.5 \times 10^6$ | $8.7 \times 10^4$ | III |
| AAV-A161LH/GLS | $4.0 \times 10^6$ | $8.0 \times 10^7$ | $3.4 \times 10^4$ | III |
| AAV-A312 | $1.8 \times 10^6$ | — | $5.3 \times 10^2$ | III |
| AAV-N319 | $2.4 \times 10^7$ | $4.5 \times 10^5$ | $0.6 \times 10^3$ | III |
| AAV-A323-4C-RGD/GLS | (+) | — | — | I |
| AAV-A339BPV | (+) | — | — | II |
| AAV-A375BPV | — | — | — | I |
| AAV-A441 | — | — | — | I |
| AAV-A459 | $7.2 \times 10^6$ | $8.0 \times 10^7$ | $6.5 \times 10^4$ | III |
| AAV-A459BPV/GLS | $5.6 \times 10^7$ | $4.5 \times 10^6$ | $2.2 \times 10^5$ | III |
| AAV-A459LH/GLS | $3.2 \times 10^6$ | $4.5 \times 10^5$ | — | II |
| AAV-A466 | (+) | $7.5 \times 10^7$ | — | II |
| AAV-N472 | — | — | — | I |
| AAV-A480-4C-RGD/GLS | — | — | — | I |
| AAV-N496 | $22 \times 10^6$ | — | $1.1 \times 10^2$ | III |
| AAV-A520LH/GLS | (+) | $7.5 \times 10^7$ | — | II |
| AAV-A520BPV/LLA | (+) | $7.5 \times 10^7$ | — | II |
| AAV-N540 | (+) | $8.0 \times 10^7$ | — | II |
| AAV-N549 | (+) | $4.5 \times 10^6$ | — | II |
| AAV-N584 | $1.1 \times 10^8$ | $8.0 \times 10^7$ | $4.0 \times 10^5$ | III |
| AAV-A584BPV/ALS | $3.0 \times 10^7$ | $8.0 \times 10^7$ | $6.5 \times 10^2$ | III |
| AAV-A584BPV/LLA | $1.3 \times 10^7$ | $9.0 \times 10^6$ | — | II |
| AAV-A584BPV/GLS | (+) | $7.5 \times 10^7$ | — | II |
| AAV-A587BPV/ALS | $1.8 \times 10^7$ | $8.0 \times 10^6$ | $5.0 \times 10^1$ | III |
| AAV-A587BPV/LLA | $7.2 \times 10^5$ | $9.0 \times 10^5$ | — | II |
| AAV-A587BPV/GLS | $3.5 \times 10^7$ | $9.0 \times 10^7$ | $2.7 \times 10^2$ | III |
| AAV-A595-4C-RGD/GLS | — | $2.5 \times 10^4$ | — | I |
| AAV-A597-4C-RGD/GLS | — | $2.5 \times 10^4$ | — | I |
| AAV-A657 | $1.8 \times 10^7$ | $7.5 \times 10^7$ | $5.2 \times 10^4$ | III |
| AAV (wild-type) | $4.8 \times 10^7$ | $9.0 \times 10^7$ | $6.2 \times 10^5$ | N/A |

Of the sites chosen for linker insertion, 20 (80%) tolerated this manipulation as assessed by particle formation. Infectious virus could be produced containing linker insertions at twelve of the sites that were tolerated for viral assembly (12/20; 60%). This represents 48% of the sites originally selected for mutagenesis.

Although twelve sites within the AAV2 capsid protein(s) could be altered, and the mutant capsid monomers still assemble, package viral genomes, and infect cells, the infectious titers of these viruses varied greatly. These ranged from essentially wild-type levels to greater than four orders of magnitude less infectious than wild-type. Significantly, several sites could tolerate a wide range of genetic insertions without effects on virus titer. Both of the sites within the VP1/VP2 unique region of the capsid ORF proved able to tolerate genetic insertions without a loss in viral titer. See results for mutant vectors with insertions after amino acid positions A139 and A161. However, insertion after position A161 showed some dependence on surrounding sequence elements. See Example 5 below. Within the VP3 region of the capsid ORF, results were more variable. Although many insertions were tolerated with essentially no loss in vector titer (for example, after positions R459 and Q584), there was a greater dependence on linker sequences (compare AAV-N584BPV/ALS to AAV-N584BPV/LLA; also see Example 5, below) and the primary sequence of the epitope being inserted (compare AAV-A459BPV/GLS to AAV-A459LH/GLS).

EXAMPLE 2

The surface accessibility of inserted BPV epitopes in the mutant AAV vectors described in Example 1 was examined by immunoprecipitation.

Iodixanol grandient-purified vectors were precipitated with anti-BPV monoclonal antibody using protein-G Sepharose, subjected to SDS-PAGE, blotted to nylon membranes and probed with anti-AAV B1 monoclonal antibody. A summary of epitope display for each BPV insertion mutant is shown in Table 3 below.

TABLE 3

Surface Display of Inserted BPV Epitopes

| Mutant Vector Designation | Epitope Display |
|---|---|
| AAV-A139BPV/GLS | + |
| AAV-A161BPV/ALS | + |
| AAV-A161BPV/LLA | + |
| AAV-A161BPV/GLS | + |
| AAV-A339BPV | − |
| AAV-A459BPV/GLS | + |
| AAV-A520BPV/LLA | + |
| AAV-A584BPV/ALS | + |
| AAV-A584BPV/LLA | + |
| AAV-A584BPV/GLS | − |
| AAV-A587BPV/ALS | + |
| AAV-A587BPV/LLA | − |
| AAV-A587BPV/GLS | + |

Inserted peptide epitopes could be displayed efficiently on the surface of viral particles at each site tested which were all sites that insertion gave rise to infectious vectors. However, display was often dependent on inclusion of appropriate linker/scaffolding sequences.

EXAMPLE 3

The mutant AAV vectors of Example 1 were also tested for retention of the ability to bind HSPG.

The ability of the AAV vectors to bind HSPG was assessed by purifying the AAV preparations on an iodixanol gradient. The 40% iodixanol layer was collected and diluted in PBS-MK containing heparin sulfate affinity resin. The mixtures were incubated for two hours with gentle shaking at 4° C. followed by centrifugation. The viral bound resin was washed three times with PBS-MK for ten minutes at room temperature and resuspended in loading buffer. The samples were then boiled and analyzed by Western blotting with monoclonal antibody B1 directed against the AAV2 VP3 capsid protein.. A summary of the HS-binding characteristic for all of the mutant is presented in Table 4 below.

TABLE 4

HSPG Binding

| Mutant Vector Designation | HSPG Binding |
|---|---|
| AAV-A26 | − |
| AAV-A46 | + |
| AAV-A115-4C-RGD/GLS | + |
| AAV-A139 | + |
| AAV-A139BPV/GLS | + |
| AAV-A139LH/GLS | + |
| AAV-A161BPV/ALS | + |
| AAV-A161LH/GLS | + |
| AAV-A312 | − |
| AAV-A323-4C-RGD/GLS | − |
| AAV-A375BPV | + |
| AAV-A459 | + |
| AAV-A459LH/GLS | + |
| AAV-A466 | + |
| AAV-N472 | + |
| AAV-A480-4C-RGD/GLS | + |
| AAV-A520LH/GLS | − |
| AAV-A520BPV/LLA | − |
| AAV-A540 | + |
| AAV-N549 | − |
| AAV-A584BPV/ALS | + |
| AAV-A584BPV/LLA | + |
| AAV-A584BPV/GLS | − |
| AAV-A587BPV/ALS | + |
| AAV-A587BPV/LLA | + |
| AAV-A587BPV/GLS | + |
| AAV-A595-4C-RGD/GLS | + |
| AAV-A597-4C-RGD/GLS | + |
| AAV (wild-type) | + |

Some of the Type II mutants may have been non-infectious because they no longer bound HSPG (see the A26 or A520 mutants). These mutants are valuable because the endogenous tropism of the virus has been ablated and any binding capability added to the virus would be exclusive. In situations in which loss of receptor-binding ability as a result of introducing mutations at a specific capsid site is not desirable, the foregoing data demonstrates that binding can often be rescued by inclusion of appropriate flexible linker sequences.

EXAMPLE 4

A mutant AAV2 vectors containing a peptide insertion at two different sites within the capsid protein was generated using the methods described herein. The 4C-RGD peptide (SEQ ID NO: 10) was inserted using site directed mutagenesis as described in Example I after amino acid position 520 and position 588 within the VP3 capsid protein. The double mutant AAV2 vector (denoted herein as A520RGD4C588RGD4C) was assessed for particle formation and vector infectivity. Particles were identified by ELISA using A20 monoclonal antibody, whereas DNA-containing particles were identified by dot-blot. Vector particles were tested for infectivity by cellular tranduction assay on Adenovirus-infected C12 cells. The double mutant was able to infect cells and produce viral particles at a similar rate as other mutant and wild-type vectors. In Table 5, infectivity is presented as the percentage of target cells expressing the vector-encoded transgene and particle titer is presented as particles/µl.

TABLE 5

| Capsid | Infectivity | HS Binding | Particle Titer A20 ELISA | DNA Dot Blot |
|---|---|---|---|---|
| A520RGD4C | – | – | $7.5 \times 10^4$ | – |
| A588RGD4C | 52.1% | + | $7 \times 10^5$ | $8 \times 10^4$ |
| A520RGD4C588RGD4C | 45.8% | – | $2 \times 10^5$ | $5 \times 10^4$ |
| ACG | 49.9% | + | $1 \times 10^6$ | $2 \times 10^5$ |

The ability of the double mutant AAV capsids to bind HSPG was assessed as describe in Example 3. The double mutant was unable to bind to HSPG like the A520RGD4C vector, but retained the ability to infect the target cells similar to A5884RGD4C. See Table 9 above. Thus, the double mutant, A520RGD4C588RGD4C, is a receptor-targeted mutant that was produced at a reasonable titer and is defective in binding the AAV2 endogenous receptor HSPG.

EXAMPLE 5

It was envisioned that insertion of larger peptide epitopes might disrupt the AAV capsid by conformationally straining neighboring sequences. To circumvent this problem, two different approaches were employed in generating various mutant AAV packaging plasmids described in Example 1. First, in some altered capsids the structure of neighboring capsid regions was maintained by the introduction of a disulfide bond, and second, in other altered capsids flexible linker sequences were included to minimize conformational stress. See Table 6 below, wherein linker sequence TG-ALS indicates that linker amino acids TG were included at the amino terminus of the inserted epitope and amino acids ALS were included at the carboxy terminus of the inserted epitope.

TABLE 6

Dependence on Appropriate Linker/Scaffolding Sequences

| Mutant Vector Designation | Linker Sequence | Particle Titer | Infectious Titer | HSPG Binding | Epitope Display | Type |
|---|---|---|---|---|---|---|
| AAV-A161BPV/ALS | TG-ALS (SEQ ID NO: 7) | ++++ | ++++ | + | + | III |
| AAV-A161BPV/LLA | TG-LLA (SEQ ID NO: 8) | ++ | ++ | + | + | III |
| AAV-A161BPV/GLS | TG-GLS (SEQ ID NO: 9) | +++ | ++++ | + | + | III |
| AAV-N584BPV/ALS | TG-ALS (SEQ ID NO: 7) | ++++ | ++++ | + | + | III |
| AAV-N584BPV/LLA | TG-LLA (SEQ ID NO: 8) | +++ | – | + | + | II |
| AAV-N584BPV/GLS | TG-GLS (SEQ ID NO: 9) | + | – | – | – | II |
| AAV-A587BPV/ALS | TG-ALS (SEQ ID NO: 7) | +++ | +++ | + | + | III |
| AAV-A587BPV/LLA | TG-LLA (SEQ ID NO: 8) | ++ | – | + | – | II |
| AAV-A587BPV/GLS | TG-GLS (SEQ ID NO: 9) | ++++ | ++ | + | + | III |

Through the choice of appropriate linkers, infectious virus was rescued from previously dead mutants. In other instances, titers were influenced over several orders of magnitude. From this analysis it is clear that incorporation of flexible linkers containing small uncharged amino acids (such as alanine or serine) is extremely important for rescuing virus structure, infectivity, and for efficient epitope display.

EXAMPLE 6

The ability of vector AAV-A139LH (containing the LH receptor binding peptide) to target the human ovarian cancer cell line OVCAR-3 was tested. Expression of the LH receptor is upregulated on these cells. Because OVCAR-3 cells also express HSPG control experiments were performed to demonstrate that the AAV vector indeed exhibited an altered tropism.

Briefly, equal numbers of AAV-A139LH vector particles or vector particles with BPV inserts instead of LH inserts were applied to the surface of OVCAR-3 cells for 2 hours at 4° C. HeLa cells which express HSPG but not the LH receptor were used as a control cell line. Experiments were performed either in the presence or absence of 500 µg/ml soluble heparin sulfate (HS) which competes with binding between AAV and HSPG and in the presence or absence of progesterone which increases expression of the LH receptor. The cells were then washed of unbound vector, shifted to 37° C. and maintained for 48 hours at which time gene transfer was assessed.

In the experiments, AAV-A139LH transduced both HeLa and OVCAR-3 cells in the absence of HS. In the presence of HS, transduction of OVCAR-3 cells was reduced more than 10-fold and transduction of Hela cells was reduced more than 100-fold. Addition of progesterone restored transduction of ovarian cells that was lost in the presence of HS. The addition of progesterone increased transduction of OVCAR-3 cells by AAV-A139LH but not by AAV-A139BPV.

These results demonstrate that AAV-A139LH has acquired tropism for cells expressing the LH receptor.

As demonstrated by the foregoing data, AAV vectors of the invention may therefore be used for targeted DNA delivery. Some indications include: cancer gene therapy (e.g., for toxin or "suicide" gene delivery) and therapeutic gene transfer to cell and/or tissue types that have been refractive to gene transfer with conventional AAV vectors (e.g., airway epithelium for the treatment of cystic fibrosis, glia for the treatment of primary brain cancers, and hematopoietic progenitors cells for the treatment of any number of other disorders). For therapeutic gene delivery, AAV vectors of the invention may be targeted to non-antigen presenting cells in order to avoid an immune response to a gene or protein of interest and/or may incorporate epitope shielding moieties and/or mutations of immunodominant epitopes.

Alternatively, AAV vectors may be used as vaccines. Viral particles containing foreign epitopes may be used directly as immunogns. AAV vectors displaying such epitopes may also contain DNA that would lead to the expression of the same or related sequences within target cells. Such a dual immunization approach is contemplated to generate a more robust and wider range response. For vaccine use, targeted AAV vectors may specifically transduce APC (while avoiding other cells).

Finally, AAV vectors of the invention may be used as non-therapeutic reagents such as imaging reagents for the determination of vector pharmokinetics and biodistribution, for example, through the attachment of radio tracer elements and real-time scintography.

EXAMPLE 7

Fourteen additional AAV capsid mutants were generated in the non-infectious AAV plasmid, pACG, by PCR-based site-directed mutagenesis as described in Example 1. In all thirteen, the 4C-RGD peptide (CDCRGDCFC; SEQ ID NO: 10) was inserted into the AAV capsid monomer.

4C-RGD encoding oligonucleotide were inserted into seven different sites within the AAV capsid gene. One site was within the VP1 unique region of the AAV2 capsid protein gene, three were within the VP1/VP2 unique region, and the three remaining sites were located within the VP3 region of the capsid ORF. DNA encoding the 4C-RGD peptide epitope was either inserted alone or flanked by one of two different five amino acid connecting peptide linkers, as described in Example 5. See Table 7 below. Producer cell lines based on 293 cells were used to generate modified AAV vectors comprising the altered capsids. These modified vectors are denoted as "AAV-RGD" collectively herein.

TABLE 7

| Vector Designation | Upstream Linker | Inserted Peptide (SEQ ID NO: 10) | Downstream Linker | Particle Titer (ELISA) |
|---|---|---|---|---|
| A46-RGD4C | TG | CDCRGDCFC | — | $8.5 \times 10^7$ |
| A46-RGD4CGLS | TG | CDCRGDCFC | GLS | $4.5 \times 10^6$ |
| A115-RGD4C | TG | CDCRGDCFC | — | $4.5 \times 10^6$ |
| A115-RGD4CGLS | TG | CDCRGDCFC | GLS | $6.0 \times 10^7$ |
| A139-RGD4C | TG | CDCRGDCFC | — | $8.5 \times 10^7$ |
| A139-RGD4CGLS | TG | CDCRGDCFC | GLS | $9.0 \times 10^7$ |
| A161-RGD4C | TG | CDCRGDCFC | — | $4.5 \times 10^6$ |
| A161-RGD4CALS | TG | CDCRGDCFC | ALS | $5.0 \times 10^6$ |
| A459-RGD4C | TG | CDCRGDCFC | — | $4.5 \times 10^6$ |
| A459-RGD4CGLS | TG | CDCRGDCFC | GLS | $4.5 \times 10^6$ |
| A584-RGD4C | TG | CDCRGDCFC | — | $8.5 \times 10^7$ |
| A584-RGD4CALS | TG | CDCRGDCFC | ALS | $9.0 \times 10^7$ |
| A588-RGD4C | TG | CDCRGDCFC | — | $9.0 \times 10^7$ |
| A588-RGD4CGLS | TG | CDCRGDCFC | GLS | $9.0 \times 10^7$ |
| Wild-type | — | — | — | $7.5 \times 10^7$ |

All the mutant capsid proteins were efficiently assembled and packaged. Furthermore, all of the modified AAV vectors generated were infectious, although there were significant differences in their efficiency of mediating gene transduction. See Table 8 below.

TABLE 8

| | Percent eGFP Positive Cells | |
|---|---|---|
| Capsid | rAVVeGFP (alone) | rAVVeGFP (+500 µg/ml Heparin Sulfate) |
| A46-RGD4C | 2.5% | 1% |
| A46-RGD4CGLS | 3.% | 0.5% |
| A115-RGD4C | 5% | 1% |
| A115-RGD4CGLS | 7.5% | 1% |
| A139-RGD4C | 35% | 2.5% |
| A139-RGD4CGLS | 40% | 2% |
| A161-RGD4C | 4% | 0.5% |
| A161-RGD4CALS | 5% | 1% |
| A459-RGD4C | 3.5% | 1% |
| A459-RGD4CGLS | 3% | 0.25% |
| A584-RGD4C | 49% | 30% |
| A584-RGD4CALS | 51% | 37% |
| A588-RGD4C | 40% | 32% |
| A588-RGD4CGLS | 46% | 38% |
| Wild-type | 47.5% | 1% |

The differences in gene transduction among the AAV-RGD vectors were related to both the site of peptide insertion and the presence, or absence, of linker sequences flanking the inserted 4C-RGD peptide. Insertion of the RGD epitope following AAV VP1 amino acids at positions 46, 115, 161 or 459 severely diminished infectious titer. However, insertions following the AAV amino acids at positions 139, 584 and 588 were well tolerated and did not affect titer appreciably.

For all the AAV-RGD vectors, inclusion of linker/scaffolding sequences resulted in slightly more efficient infection and maintenance of titer. To determine if the inserted 4C-RGD peptide had imparted to the modified vectors HSPG-independence, gene transduction assays were performed in the presence of heparin sulfate as described in Example 5. Although, AAV vectors containing unmodified capsids were unable to transduce cells in the presence of heparin sulfate, AAV-RGD vectors containing the 4C-RGD epitope following amino acids 584 and 588 transduced all types of cells tested in the presence of heparin sulfate. These results strongly suggest that AAV-RGD vectors set out in Table 6 are infecting cells via a HSPG-independent mechanism.

EXAMPLE 8

To assess if the AAV-RGD viral particles bind integrin receptors, a solid-phase ELISA assay using purified $\alpha_v\beta_3$ integrin was carried out as follows.

Neutravidin-coated plates (Pierce, Rockford, Ill.) were incubated with 1 µg/well of biotinylated heparin in PBST (0.05% Tween 20, 0.2% BSA) overnight at 4° C. The wells were then washed five times with wash buffer (PBS containing 0.05% Tween-20 and 0.1 % BSA) and AAV particles were bound at room temperature for two hours with gentle shaking. Subsequently, the plate was washed five times with wash buffer and purified integrin $\alpha_v\beta_3$ (Chemicon, Temecula, Calif.) in binding buffer (20 mM Tris-HCl , 150 mM NaCl , 2 mM $CaCl_2$. 1 mM $MgCl_2$. 1 mM $MnCl_2$ and 0.1% BSA, pH 7.5) was added to each well at a concentration of 1 µg/ml. The plates were incubated overnight at 4° C., washed three times with wash buffer and incubated with VNR139 monoclonal antibody (anti-$\alpha_v$ subunit, GIBCO-BRL; Gaithersburg, Md.) in binding buffer for 2 hours at room temperature. The plates are then washed five times and incubated with secondary antibody (HRP-conjugated anti-mouse IgG) for 1 hour at room temperature. Following a final wash the ELISA plate was developed with ABTS substrate solution and the VECTASTAIN kit (Vector Laboratories, Burlingame, Calif.) as recommended by the manufacturer. Color development was stopped by the addition of 1N $H_2SO_4$, and plates were read in a plate reader set at 405 nM.

This analysis clearly indicated that the AAV-RGD viral particles bound $\alpha_v\beta_3$ integrin. The unmodified viral particles bound only at background level at all concentrations tested.

EXAMPLE 9

The insertion of the RGD peptide in the capsid protein of AAV-RGD vectors modified the cellular tropism of these vectors. The cell entry pathway of the AAV RGD vectors was investigated by measuring gene transfer to cell lines expressing various levels of HSPG as well as intergrins $\alpha_v\beta_3$ and $\alpha_v\beta_5$. The following cell lines were tested: Hela cells, K562 human chronic myelogenous leukemia cells and Raji human lymphoblast-like cells.

First, flow cytometry was used to analyze the integrin and HSPG expression profile of these cell lines. Briefly, the cells were resuspended in SM buffer (HEPES-buffered saline containing 1% bovine serum albumin) at $2\times10^6$ cell/ml. The cells were incubated briefly at 37° C. to allow regeneration of surface integrins, then incubated with FITC-labeled LM609 antibody or FITC-labeled PIF6 antibody (1:200 dilution, Chemicon, Temeula, Calif.) for two hours at 4° C. HSPG expression in these cells was analyzed with anti-HSPG monoclonal antibody, HepSS-1 (1:200 dilution) for two hours at 4° C. Subsequently the cells were washed five times with SM buffer and incubated with FITC labeled goat anti-mouse IgM serum (1:800 dilution) for one hour at 4° C., the cells were washed with SM buffer and analyzed by flow cytometry. This analysis demonstrated that Hela cells expressed high levels of HSPG and $\alpha_v\beta_5$ integrin and low levels of $\alpha_v\beta_3$ integrin. K562 cells expressed low levels of HSPG, but $\alpha_v\beta_5$ integrin was expressed at high levels. Raji cells were negative for HSPG expression and expressed high levels of $\alpha_v\beta_3$ and $\alpha_v\beta_5$ integrins. Subsequently, the ability of the wild-type AAV-eGFP and the modified vectors (A584-RGD4C-eGFP, A584-RGD4CALS-eGFP, A588-RGD4C-eGFP, A588-RGD4CGLS) to transfer the eGFP gene to Hela, Raji and K562 cells was analyzed. The cells were seeded in a 24-well plates the day prior to infection in order to reach 75% confluence or about $5\times10^5$ cell/ml on the following day. Serial dilutions of the vectors were added to the cells in the presence of Ad5 at the MOI of 3iu/cell. The cells and viruses were incubated at 37° C. for 48 hours, after which the media was removed and the cells washed two time with PBS. The cells were then fixed and analyzed for GFP transduction by FACS analysis using an anti-GFP antibody.

Due to the low expression of HSPG, K562 and Raji cells were poorly transduced by AAVeGFP vectors containing unmodified AAV capsid protein, but these cells were efficiently transduced by the same vector packaged into A5884C-RGD capsids. The efficiency of eGFP gene transduction by was similar to that observed by the unmodified AAV vector in Hela cells. Furthermore, gene transfer mediated by the RGD-containing particles was 4-fold higher in the K562 cells and 13-fold higher in the Raji cells as compared to transduction by vectors comprising unmodified capsids. These experiments clearly demonstrate that incorporation of the 4C-RGD epitope into the VP3 monomer of AAV2 vectors resulted in dramatic changes in the initial steps of virus-cell interaction, presumably by creating an alternative cell attachment and entry pathway.

Experiments were also carried out to compare the binding profiles of the wild type AAV2 vector and that containing the 4C-RGD capsid protein using soluble heparin sulfate to compete for binding, and anti-AAV monoclonal antibody A20 and FACS analysis to detect binding. In these experiments, wild type AAV2 vector did not bind to Hela cells in the presence of heparin sulfate. However, vectors containing A5884C-RGD capsid protein bound to Hela cells in the presence of soluble heparin sulfate. Binding of modified AAV viral particles to Hela cells was blocked by treatment with synthetic RGD peptide. Since the RGD peptides could efficiently block binding, these data further suggest that AAV-RGD capsids use cellular integrins as receptors during the cell attachment process.

EXAMPLE 10

Experiments were carried out to determine if the AAV-RGD vectors were capable of mediating gene delivery via integrin receptors.

Competitive inhibition assays using soluble heparin sulfate to inhibit AAV-mediated gene delivery were carried out as follows. AAV-RGD vectors or control vector AAVeGFP and modified vectors A584-RGD4C-eGFP, A584-RGD4CALS-eGFP, A588-RGD4C-eGFP, A588-RGD4CGLS were first incubated with 1500 µg/ml soluble heparin sulfate for two hours at 37° C. and then incubated with the Hela cells at 4° C. in the presence of 500 µg/ml heparin sulfate for an additional four hours. The cells were subsequently washed three times with fresh medium to remove unbound vector and incubated for 48 hours at 37° C., after which the cells were washed two times with PBS, fixed and analyzed for GFP gene transduction by FACS analysis in Hela cells.

When infected with the control virus, AAVeGFP comprising the unmodified capsid, GFP gene expression in Hela cells was efficiently blocked by soluble heparin sulfate. The same concentrations of heparin sulfate only blocked about 20% of A5884C-RGD capsid-mediated GFP expression in Hela cells. These experiments further demonstrated that the A5884-RGD capsids were capable of using an alternative HSPG-independent cell entry pathway.

To assess the specificity of the alternate cell entry pathway through integrin receptor, synthetic RGD peptide (200 μg/ml) or anti-integrin antibody VNR139 was used to determine if AAV-RGD mediated gene-transduction was inhibited in the presence of soluble heparin sulfate. The addition of the RGD specific inhibitor in combination with heparin sulfate completely inhibited A5884C-RGD-mediated gene expression. This experiment demonstrated that the HSPG-independent interaction was due to interaction with RGD-binding integrins expressed on the Hela cells.

EXAMPLE 11

The ability of unmodified AAV vector (wild type) to mediate GFP gene transduction was tested in various ovarian adenocarcinoma cell lines. Transduction of the eGFP gene was measured by FACS. Unmodified AAV vector mediated gene transfer and expression in the human ovarian adenocarcinoma cell lines PA-1, OVCAR-3, OVCAR-3N and OV4. Unmodified AAV vector did not transduce the ovarian adenocarcinoma cell lines Hey, SKOV-3 and OV3. The unmodified AAV vector transfers the eGFP gene via the HSPG receptor. HSPG expression in ovarian cancer cells was determined by FACS analysis using an anti-HSGP antibody (Seikagaku America, Falmouth, Mass.). The unmodified AAV vector was unable to transduce the Hey and OV3 cell line since these cell lines were negative for HSPG expression. See Table 8.

Since some human ovarian adenocarcinoma cell lines do not express HSPG, it was of interest to determine if ovarian tumor antigens (e.g., integrin) would facilitate AAV-mediated gene transfer in ovarian cancer cells. Integrin expression was analyzed by FACS analysis using an anti-$\alpha_v$ antibody and the data is displayed in Table 9. All ovarian cancer cells tested expressed a member of the $\alpha_v$ integrin family.

TABLE 9

Integrin and HSPG Expression on Human Ovarian Adenocarcinoma

| Ovarian Adenocarcinoma | HSPG Expression | $\alpha_v$ Integrin Expression |
|---|---|---|
| PA-1 | + | + |
| Hey | − | + |
| OVCAR-3 | + | + |
| OVCAR-3N | + | + |
| OV4 | + | + |
| SKOV-3ip | − | + |
| OV3 | − | + |

The AAV-RGD vectors A588-RGD4C-eGFP and A588-RGD4CGLS were tested for their ability to target gene transfer to the ovarian cell lines as described in Example 9. These AAV-RGD vectors were able to transduce all ovarian cancer cell lines tested. The AAV-RGD vectors were able to more efficiently direct gene transfer in the ovarian cell lines PA-1, Hey, OVCAR-3, OVCAR-3N, OV4, SKOV-3ip and OV3 in comparison compared to wild-type AAV vector containing unmodified capsid.

AAV-RGD mediated gene transfer was demonstrated to be independent of HSPG interaction. Competitive gene transfer experiments in the OVCAR-3 cell line were carried out with soluble heparin sulfate as described in Example 10. A5884C-RGD vector efficiently directed gene transfer in the presence of soluble heparin sulfate in OVCAR-3 cells. However, gene transfer was completely blocked by the addition of RGD peptide or anti-integrin antibody in the presence of soluble heparin sulfate. The A5884C-RGD mediated gene transfer proceeded through integrin receptors.

EXAMPLE 12

Side-by-side comparison of the effectiveness of the unmodified AAV2 vector and the RGD-AAV vector for gene transfer to ovarian tumors was carried out in vivo. Human SKOV-3 cells were delivered intraperitoneally into SKID mice and developed tumors in the peritoneal cavity five days after implantation. The tumors were allowed to develop for five-seven days. Subsequently, matched doses of AAV-RGD vector or unmodified AAV vectors engineered to express the eGFP gene were administered intraperitoneally to the mice at $5\times10^8$ particles/mouse. At 15, 25, and 35 days post vector administration, the mice were sacrificed and the tumors were analyzed for the extent of gene delivery and expression. eGFP expression was detected in paraffin sections of tumor tissue using an anti-GFP antibody. In Table 10, GFP gene expression is indicated as a percent of tumor tissue expressing the gene, AAV-RGD indicates tumor tissue harvested from mice treated with AAV-RGD vector and ACG indicates tumor tissue harvested from mice treated with wild type vector.

TABLE 10

| | GFP Expression | |
|---|---|---|
| Day | AAV-RGD | ACG |
| 15 | 15% | 3% |
| 25 | 60% | 7% |
| 35 | 95% | 7% |

It is generally accepted that for an anti-tumor gene therapy to be effective a genetic vector must be able to deliver and express a gene in as much of the tumor as possible. In studies with other transgenes, (e.g., HSV-TK) it has been established that at least 10–15% of the tumor needs to be transduced in order to be effective. This experiment suggest that the unmodified AAV2-vectors would not be effective anti-tumor agents since the transduction rate in vivo was low. In contrast, the modified RGD-AAV vector had a high rate of gene transduction and therefore may an excellent candidate for anti-tumor therapy. The fact that the eGFP expression comes on slowly (increasing over a 5 week period) is not unexpected and is a characteristic of rAAV.

EXAMPLE 13

In addition to inserting peptide ligands into the AAV2 vector to modify viral tropism, peptide insertions in the AAV2 vector can also be used as substrates for an enzymatic reaction covalently linking a biotin molecule in a site-specific manner to the AAV capsid. AAV capsids have been engineered to include a unique fifteen amino acid long biotin acceptor (BAP) peptide that is recognized by an *E. coli* enzyme, biotin protein ligase. In the presence of ATP, the ligase specifically attaches biotin to the lysine residue in this sequence. When the bacterial enzyme was expressed in a packaging cell line where AAV vector biosynthesis was occurring, vector capsid proteins were biotinylated as they were made and assembled into viral particles. The result of such a packaging scheme was in vivo biotinylated AAV particles. The advantages to labeling the AAV vector by biotinylation is that the reaction is enzymatic and therefore the conditions are gentle and the labeling is highly specific.

The AAV-BAP vectors were generated by methods similar to those described for the AAV-BPV, AAV-LH and AAV-RGD vectors in Example 1. Six AAV-mutants were generated and the packaging plasmids encoding these mutants are designated herein as pAB139BAP/ALS, pAB139BAP/GLS, pAB161BAP/ALS, pAB161BAP/GLS, pAB584BAP/GLS, and pAB584BAP/ALS. These mutants contain BAP insertions of the peptide sequence (GLNDIFEAQKIEWHE; SEQ ID NO: 11) flanked by either TG-ALS, or TG-GLS linker sequence (SEQ ID NO: 7 and 9, respectively). BAP insertions within the AAV vector following amino acids at positions 139 and 161 (regardless of the linker sequence) produced infectious mutant AAV vector particles at a level similar to wild-type. Insertion of the BAP peptide following amino acid 584 with the GLS linker causes a slight, but insignificant (less than 10-fold), decease in particle titer. Insertion of the BAP peptide at the same site within the AAV vector with the ALS linker caused a significant (>10,00 fold) decrease particle titer. All of the insertion sites within the AAV vector contemplated by the present invention (positions 139 and 161 in the VP1/VP2 region and positions 459, 584, 588 and 657) are candidate sites for the BAP insertion.

EXAMPLE 14

In order to label the AAV particles containing the BAP insert with biotin, a system for expressing the biotin ligase (BirA) enzyme in a packaging cell line was developed to create an in vivo biotinylated AAV vector. The BirA gene was inserted into the pCMV plasmid and is designated herein as pCMV-BirA. This plasmid was used to direct BirA gene expression in 283 cells and used with the AAV-BAP vector to produce in vivo biotinylated AAV vector. Briefly, 293 cells were transfected with the pCMV-BirA plasmid with a selectable maker gene (Neo). The resulting packaging cell was stably transfected with a rAAV comprising a DNA of interest flanked by AAV inverted terminal repeats, an AAV helper construct containing cap gene with a mutant BAP insertion (Example 12), an adenovirus helper plasmid or infected with adenovirus. Alternatively, 293 cells (which are standard AAV vector packaging cells) stably transfected with pCMV-BirA may be used as the packaging cell line. In addition, 293 cells infected with the adenovirus engineered to express the BirA gene may be used as the packaging cell line. AAV particles containing capsids with BAP insertions can also be labeled in vitro (post-purification) using purified BirA enzyme (available commercially).

Alternatively, a recombinant replication-competent adenovirus that expresses BirA was also developed for biotinylated AAV vector synthesis, eliminating the need for a separate BirA expression plasmid. This system allowed for large-scale AAV vector production of the biotinylated AAV utilizing packaging cell lines that have integrated copies of both AAV vector and AAV helper sequences. The Ad-based BirA expression system also was able to drive the expression of much larger amounts of the BirA gene product. The adenovirus expressed a BirA-eGFP fusion protein from a CMV promoter in the Ad E3 region, which allowed for monitoring BirA expression via GFP fluorescence.

A sensitive ELISA assay was used to quantitate the extent and efficiency of in vivo (and/or in vitro) biotinylation. AAV containing the 584BAP/GLS insertion was shown to be efficiently biotinylated in vivo (and in vitro) using either the plasmid based or Ad-based BirA expression systems. The biotinylated AAV vectors when conjugated to biotinylated ligands (e.g., monoclonal antibodies) via strepavidin can be specifically targeted to cell surface receptors of interest.

The advantages of using the biotinylation reaction to label the AAV viral particles is that it is an enzymatic reaction and therefore the conditions are gentle while the labeling is highly specific. In addition, the in vivo biotinylation reaction described herein has a much higher biotinylation efficiency than chemical biotinylation utilizing cross-linking reagents.

The biotinylated AAV viral particles are contemplated to serve as substrates for conjugation of targeting motifs (e.g., monoclonal antibodies, growth factors, cytokines) to the surface of vector particles through utilizing avidin/strepavidin-biotin chemistry. In addition, the biotinylated AAV viral particles are contemplated to be useful for visualizing the biodistribution of the viral particles both in vivo and in vitro. The biotinylated viral particles can be visualized with fluorescence or enzymatically with labeled strepavidin compounds. Biotinylation may also be useful for conjugating epitope shielding moieties, such as polyethylene glycol, to the AAV vector. The conjugation of shielding moieties will allow the vector to evade immune recognition. Biotinylation of the AAV vector is also contemplated to enhance intracellular trafficking of viral particles through conjugation of proteins or peptides such as nuclear transport proteins. Biotinylation may also be use to conjugate proteins or peptides which effect the processing of AAV vector genomes such as increasing the efficiency of integration. In addition, biotinylation may also be used to conjugate proteins or peptides that effect the target cells, e.g., proteins that make a target cell more susceptible to infection or proteins that activate a target cell thereby making it a better target for the expression of a therapeutic or antigenic peptide.

While the present invention has been described in terms of preferred embodiments, it understood that variations and improvements will occur to those skilled in the art. Therefore, only such limitations as appear in the claims should be placed on the invention.

What is claimed is:

1. An AAV2 vector comprising a capsid protein with a peptide insertion at a position selected from the group consisting of:
   (a) position 139 in the VP1 capsid (SEQ ID NO: 13) and
   (b) position 161 in the VP1 capsid (SEQ ID NO: 13).

2. The AAV2 vector of claim 1 wherein said position is position 139.

3. The AAV2 vector of claim 1 wherein said position is position 161.

4. An AAV2 vector comprising a capsid protein with a peptide insertion at a position selected from the group consisting of:
   (a) position 459 in the VP1 capsid (SEQ ID NO: 13);
   (b) position 584 in the VP1 capsid (SEQ ID NO: 13);
   (c) position 588 in the VP1 capsid (SEQ ID NO: 13); and
   (d) position 657 in the VP1 capsid (SEQ ID NO: 13).

5. The AAV2 vector of claim 4 wherein said position is position 459.

6. The AAV2 vector of claim 4 wherein said position is position 584.

7. The AAV2 vector of claim 4 wherein said position is position 588.

8. The AAV2 vector of claim 4 wherein said position is position 657.

9. The AAV2 vector of claim 1, 2, 3, 4, 5, 6, 7 or 8 wherein the peptide insertion comprises a targeting peptide.

10. The AAV2 vector of claim 9 wherein the targeting peptide comprises the amino acids CDCRGDCFC (SEQ ID NO: 10).

11. The AAV2 vector of claim 1, 2, 3, 4, 5, 6, 7, 8 or 10 wherein the insertion is flanked by a linker/scaffolding sequence.

12. An AAV2 vector of claim 11, wherein the linker/scaffolding sequence comprises the amino acids TG amino terminal to the insertion and ALS carboxy terminal to the insertion.

13. An AAV2 vector of claim 11 wherein the linker/scaffolding sequence comprises the amino acids TG amino terminal to the insertion and LLA carboxy terminal to the insertion.

14. An AAV2 vector of claim 11 wherein the linker/scaffolding sequence comprises the amino acids TG amino terminal to the insertion and GLS carboxy terminal to the insertion.

15. The AAV2 vector of claim 9 wherein the peptide insertion is flanked by a linker/scaffolding sequence.

16. An AAV2 vector of claim 15, wherein the linker/scaffolding sequence comprises the amino acids TG amino terminal to the insertion and ALS carboxy terminal to the insertion.

17. An AAV2 vector of claim 15 wherein the linker/scaffolding sequence comprises the amino acids TG amino terminal to the insertion and LLA carboxy terminal to the insertion.

18. An AAV2 vector of claim 15 wherein the linker/scaffolding sequence comprises the amino acids TG amino terminal to the insertion and GLS carboxy terminal to the insertion.

19. A polynucleotide encoding an AAV2 capsid protein with a peptide insertion at a position selected from the group consisting of: position 139 in the VP1 capsid (SEQ ID NO:13), position 161 in the VP1 capsid (SEQ ID NO:13), position 459 in the VP1 capsid (SEQ ID NO:13), position 584 in the VP1 capsid (SEQ ID NO:13), position 588 in the VP1 capsid (SEQ ID NO:13) and position 657 in the VP1 capsid (SEQ ID NO:13).

20. A cell transfected with the polynucleotide of claim 19.

21. A method of producing AAV2 vector comprising a capsid protein with a peptide insertion, comprising growing a packaging cell and providing the packaging cell with helper virus functions, wherein said packaging cell comprises the polynucleotide of claim 19, the AAV2 rep gene and a recombinant AAV2 genome comprising DNA of interest flanked by AAV2 inverted terminal repeats.

22. The method of claim 21 wherein said cell expresses biotin ligase.

23. The method of claim 21 further comprising the step of treating said AAV2 vector produced with biotin ligase.

24. An immunogenic composition comprising the AAV2 vector of claim 11.

25. A method for eliciting an immune response in an animal, said method comprising administering to the animal an immunogenic composition of claim 24.

* * * * *

UNITED STATES PATENT AND TRADEMARK OFFICE
CERTIFICATE OF CORRECTION

PATENT NO.         : 6,962,815 B2               Page 1 of 1
APPLICATION NO. : 10/038972
DATED              : November 8, 2005
INVENTOR(S)        : Jeffrey S. Bartlett It is certified that error appears in the above-identified patent and that said Letters Patent is hereby corrected as shown below:

On the Title Page:

Item (73), "Hopital" should be -- Hospital --.

Signed and Sealed this

Tenth Day of April, 2007

JON W. DUDAS
*Director of the United States Patent and Trademark Office*